US012220272B2

(12) United States Patent
Butler et al.

(10) Patent No.: US 12,220,272 B2
(45) Date of Patent: Feb. 11, 2025

(54) MOTION-COMPENSATED WAVELET ANGIOGRAPHY

(71) Applicants: AngioWave Imaging, Inc., Concord, MA (US); William E. Butler, Boston, MA (US)

(72) Inventors: William E. Butler, Boston, MA (US); Hector Andrade-Loarca, Berlin (DE)

(73) Assignee: Angiowave Imaging, Inc., Concord, MA (US)

( * ) Notice: Subject to any disclaimer, the term of this patent is extended or adjusted under 35 U.S.C. 154(b) by 724 days.

(21) Appl. No.: 17/318,313

(22) Filed: May 12, 2021

(65) Prior Publication Data

US 2022/0361834 A1    Nov. 17, 2022

(51) Int. Cl.
*A61B 6/00* (2024.01)
*A61B 6/46* (2024.01)
(Continued)

(52) U.S. Cl.
CPC ............ *A61B 6/5217* (2013.01); *A61B 6/504* (2013.01); *A61B 6/507* (2013.01); *G06T 7/0016* (2013.01);
(Continued)

(58) Field of Classification Search
CPC ..................................................... A61B 6/504
See application file for complete search history.

(56) References Cited

U.S. PATENT DOCUMENTS 3,335,716 A    8/1967  Alt
5,628,980 A    5/1997  Ranganathan et al.
(Continued)

FOREIGN PATENT DOCUMENTS

CN    101406392 B    5/2011
EP       1322219 B1    5/2007
(Continued)

OTHER PUBLICATIONS

Nielsen, Conditions for A Class of Entanglement Transformations, Aug. 17, 1999, pp. 1-4 (Cornell University Archive, arXiv No. quant-ph/9811053v2).
Novotny et al., A Method of Photographing Fluorescence in Circulating Blood in the Human Retina, Circulation, vol. XXIV, Jul. 1961, pp. 82-86.
(Continued)

*Primary Examiner* — Wen W Huang
(74) *Attorney, Agent, or Firm* — Jason M. Shapiro; Devlin Law Firm LLC

(57) ABSTRACT

Methods and systems are provided for extracting cardiac frequency angiographic phenomena for an unconstrained vascular object from an angiographic study. In one example, a computer may obtain a series of angiographic image frames obtained at a rate faster than cardiac frequency. Each image frame may comprise a plurality of pixels, and each pixel may have a corresponding intensity. The computer may apply an optical flow technique to the angiographic image frames to generate a plurality of paths corresponding to a displacement of respective pixels from image frame to image frame. The computer may further generate a spatiotemporal reconstruction of cardiac frequency angiographic phenomena based on the plurality of paths and the corresponding intensities associated with respective pixels of the paths, and output for display the spatiotemporal reconstruction of cardiac frequency angiographic phenomena in one or more images.

17 Claims, 8 Drawing Sheets

(51) Int. Cl.

| | | |
|---|---|---|
| *A61B 6/50* | (2024.01) | |
| *G06T 7/00* | (2017.01) | |
| *G06T 7/20* | (2017.01) | |
| *G06T 7/70* | (2017.01) | |
| *G06T 11/00* | (2006.01) | |
| *G16H 10/60* | (2018.01) | |
| *G16H 30/20* | (2018.01) | |
| *G16H 30/40* | (2018.01) | |
| *G16H 40/63* | (2018.01) | |
| *G16H 50/20* | (2018.01) | |
| *G16H 50/70* | (2018.01) | |

(52) U.S. Cl.
CPC ............. *G06T 7/20* (2013.01); *G06T 7/70* (2017.01); *G06T 11/005* (2013.01); *G16H 10/60* (2018.01); *G16H 30/20* (2018.01); *G16H 30/40* (2018.01); *G16H 50/70* (2018.01); *A61B 6/461* (2013.01); *G06T 2207/10016* (2013.01); *G06T 2207/30048* (2013.01); *G06T 2207/30104* (2013.01); *G16H 40/63* (2018.01); *G16H 50/20* (2018.01)

(56) References Cited

U.S. PATENT DOCUMENTS

| | | | |
|---|---|---|---|
| 5,637,871 | A | 6/1997 | Piety |
| 5,963,676 | A | 10/1999 | Wu et al. |
| 6,195,456 | B1 | 2/2001 | Balasubramanian et al. |
| 6,442,414 | B1 | 8/2002 | Watanabe |
| 6,549,801 | B1 | 4/2003 | Chen |
| 6,842,638 | B1 | 1/2005 | Suri et al. |
| 6,975,753 | B2 | 12/2005 | Matsuura et al. |
| 6,985,632 | B2 | 1/2006 | Sato et al. |
| 7,020,314 | B1 | 3/2006 | Suri et al. |
| 7,035,679 | B2 | 4/2006 | Addison et al. |
| 7,201,892 | B2 | 4/2007 | Achilefu et al. |
| 7,359,062 | B2 | 4/2008 | Chen |
| 7,602,183 | B2 | 10/2009 | Lustig et al. |
| 8,244,334 | B2 | 8/2012 | Huang et al. |
| 8,306,295 | B2 | 11/2012 | Bruder et al. |
| 8,306,303 | B2 | 11/2012 | Bruder et al. |
| 8,417,048 | B2 | 4/2013 | Reboni et al. |
| 8,559,692 | B2 | 10/2013 | Reboni et al. |
| 8,605,976 | B2 | 12/2013 | Diamant et al. |
| 8,611,633 | B2 | 12/2013 | Kwon et al. |
| 8,628,751 | B2 | 1/2014 | Neumann et al. |
| 8,948,480 | B2 | 2/2015 | Liu et al. |
| 9,019,305 | B2 | 4/2015 | Baumgart et al. |
| 9,036,780 | B2 | 5/2015 | Kyriakou et al. |
| 9,165,349 | B2 | 10/2015 | Kwon et al. |
| 9,324,005 | B2 | 4/2016 | Wadhwa |
| 9,345,413 | B2 | 5/2016 | Schie et al. |
| 9,357,916 | B2 | 6/2016 | Srivastava et al. |
| 9,811,901 | B2 | 11/2017 | Wu |
| 9,814,384 | B2 | 11/2017 | Schmoll |
| 9,836,849 | B2 | 12/2017 | Dickrell, III et al. |
| 10,123,761 | B2 | 11/2018 | Butler |
| 10,226,176 | B2 | 3/2019 | Schmoll |
| 10,299,677 | B2 | 5/2019 | Spaide |
| 10,653,379 | B2 | 5/2020 | Rapoport |
| 2004/0101090 | A1 | 5/2004 | Drummond et al. |
| 2004/0136490 | A1* | 7/2004 | Edic .................. A61B 6/4035 378/4 |
| 2005/0080327 | A1 | 4/2005 | Jenkins et al. |
| 2007/0106146 | A1 | 5/2007 | Altmann et al. |
| 2007/0106149 | A1 | 5/2007 | Mistretta |
| 2007/0185393 | A1 | 8/2007 | Zhou |
| 2008/0045847 | A1 | 2/2008 | Farag et al. |
| 2008/0205722 | A1* | 8/2008 | Schaefer ............. G06T 7/11 382/128 |
| 2008/0226149 | A1 | 9/2008 | Wischmann et al. |
| 2010/0027857 | A1* | 2/2010 | Wang ............... A61B 5/0066 382/128 |
| 2010/0113949 | A1 | 5/2010 | Sathyanarayana |
| 2010/0239147 | A1* | 9/2010 | Vitanovski ......... G06V 10/7635 382/131 |
| 2010/0272184 | A1 | 10/2010 | Fishbain et al. |
| 2011/0142288 | A1 | 6/2011 | Diamant et al. |
| 2012/0134553 | A1 | 5/2012 | Liao et al. |
| 2013/0101187 | A1 | 4/2013 | Sundar et al. |
| 2013/0116554 | A1 | 5/2013 | Kaiser et al. |
| 2013/0243348 | A1 | 9/2013 | Goshen et al. |
| 2014/0005563 | A1 | 1/2014 | Ramanathan et al. |
| 2014/0044330 | A1 | 2/2014 | Klingenbeck |
| 2014/0072190 | A1 | 3/2014 | Wu et al. |
| 2014/0072228 | A1 | 3/2014 | Rubinstein |
| 2014/0072229 | A1 | 3/2014 | Wadhwa et al. |
| 2014/0378795 | A1 | 12/2014 | McKenna |
| 2015/0045684 | A1 | 2/2015 | Schie |
| 2015/0190533 | A1 | 7/2015 | Newton et al. |
| 2015/0257653 | A1 | 9/2015 | Hyde et al. |
| 2016/0135775 | A1 | 5/2016 | Mistretta et al. |
| 2016/0189394 | A1 | 6/2016 | Zhang et al. |
| 2016/0220112 | A1 | 8/2016 | Schmoll |
| 2016/0267704 | A1 | 9/2016 | Mistretta et al. |
| 2016/0349346 | A1 | 12/2016 | Cheng |
| 2017/0000441 | A1 | 1/2017 | Butler |
| 2017/0255832 | A1* | 9/2017 | Jones ................. G06V 10/454 |
| 2017/0367603 | A1 | 12/2017 | Spector |
| 2018/0047160 | A1 | 2/2018 | Wu et al. |
| 2018/0055471 | A1 | 3/2018 | Redel |
| 2018/0333120 | A1* | 11/2018 | Wang ................. G06T 7/269 |
| 2019/0015061 | A1 | 1/2019 | Liebeskind et al. |
| 2019/0046147 | A1 | 2/2019 | Butler |
| 2019/0053780 | A1 | 2/2019 | Song et al. |
| 2019/0159683 | A1* | 5/2019 | Ma .................... G16H 30/40 |
| 2019/0159707 | A1 | 5/2019 | Albuquerque et al. |
| 2019/0209113 | A1* | 7/2019 | Liu .................... G06T 7/269 |
| 2019/0343383 | A1 | 11/2019 | Spaide |
| 2020/0125852 | A1* | 4/2020 | Carreira ............... G06N 3/049 |
| 2020/0191928 | A1* | 6/2020 | Hope Simpson ... G01S 7/52034 |
| 2020/0193597 | A1 | 6/2020 | Fan et al. |
| 2020/0222018 | A1* | 7/2020 | Van Walsum ......... A61B 6/463 |
| 2020/0245961 | A1 | 8/2020 | Butler |
| 2020/0245965 | A1 | 8/2020 | Butler |
| 2020/0286237 | A1 | 9/2020 | Butler |
| 2020/0305822 | A1 | 10/2020 | Butler |
| 2020/0320710 | A1 | 10/2020 | Butler |
| 2020/0397396 | A1 | 12/2020 | Butler |
| 2021/0137634 | A1 | 5/2021 | Lang |
| 2023/0113721 | A1* | 4/2023 | Kassel ................. G06T 7/0016 382/128 |

FOREIGN PATENT DOCUMENTS

| | | |
|---|---|---|
| JP | 2009504297 A | 2/2009 |
| WO | 2020163614 A1 | 8/2020 |
| WO | 2020163629 A1 | 8/2020 |
| WO | 2020185706 A1 | 9/2020 |
| WO | 2020198592 A1 | 10/2020 |
| WO | 2020206430 A1 | 10/2020 |

OTHER PUBLICATIONS

Pewsey et al., Circular Statistics in R, Oxford University Press, (2013) Chapters 1-3, 7 and Appendix (80 pages).

Pfister et al., Molecular diagnostics of CNS embryonal tumors, Acta Neuropathology, Nov. 2010, vol. 120, No. 5, pp. 553-566.

Pollock, Dyadic Wavelets Analysis, (2016) pp. 1-26.

Qian et al., High Resolution Stationary Digital Breast Tomosynthesis using Distributed Carbon Nanotube X-ray Source Array, Medical Physics, (Apr. 2012) vol. 39, No. 4, pp. 2090-2099.

Rashid-Farrokhi et al., Wavelet-Based Multiresolution Local Tomography, IEEE Transactions on Image Processing, Oct. 1997, vol. 6, No. 10, pp. 1412-1430.

Rollins et al., Real-time in vivo color Doppler optical coherence tomography, Journal of Biomedical Optics, Jan. 2002, vol. 7, No. 1, pp. 123-129.

(56) References Cited

OTHER PUBLICATIONS

Ronneberger et al., U-Net: Convolutional Networks for Biomedical Image Segmentation, May 18, 2015, pp. 1-8 (Cornell University Archive, arXiv No. 1505.04597v1).
Ruzhansky, Introduction to pseudo-differential operators, Jan. 21, 2014, pp. 1-54.
Sadowsky, The Continuous Wavelet Transform: A Tool for Signal Investigation and Understanding, John Hopkins APL Technical Digest, 1994, vol. 15, No. 4, pp. 306-318.
Saito et al., Efficient Gene Transfer into the Embryonic Mouse Brain Using in Vivo Electroporation, Developmental Biology, 2001, vol. 240, pp. 237-246.
Sen et al., 3D ROI Image Reconstruction from Truncated Computed Tomogrpahy, IEEE Transactions on Medical Imaging, May 26, 2013, pp. 1-24.
Shen et al., Growth hormone therapy and risk of recurrence/progression in intracranial tumors: a meta-analysis, Neurol Sci, 2015, vol. 36, pp. 1859-1867.
Shy et al., X-Y separable pyramid steerable scalable kernels, (1994) pp. 237-244 (https://authors.library.caltech.edu/3438/1/SHYcvpr94.pdf).
Valens, A Really Friendly Guide to Wavelets, 1999, pp. 1-19.
Vrhel et al., Fast Computation of the Continuous Wavelet Transform through Oblique Projections, (1996) pp. 1-4 (http://citeseerx.ist.psu.edu/viewdoc/download?doi=10.1.1.66.3780&rep=rep1&type=pdf).
Wang et al., Three dimensional optical angiography, Optics Express, Apr. 2, 2007, vol. 15, No. 7, pp. 4083-4097.
Wang et al., Doppler optical micro-angiography for volumetric imaging of vascular perfusion in vivo, May 25, 2009, Optics Express, vol. 17, No. 11, pp. 8926-8940.
Wunsch, Microlocal Analysis and Evolution Equations: Lecture Notes from 2008 CMI/ETH Summer School, 2012 (92 pages).
Yang et al., The X-Ray Transform Projection of 3D Mother Wavelet Function, Research Article, Computational and Mathematical Methods in Medicine, 2013, Article ID 754829, 9 pages.
Yazdanfar et al., High resolution imaging of in vivo cardiac dynamics using color Doppler optical coherence tomography, Optics Express, Dec. 22, 1997, vol. 1, No. 13, pp. 424-431.
Zhu et al., Endothelial nitric oxide synthase: a potential therapeutic target for cerebrovascular diseases, Molecular Brain, 2016, vol. 9, No. 30, pp. 1-8.
Zhuang et al., Fan-beam and cone-beam image reconstruction via filtering the backprojection image of differentiated projection data, Institute of Physics Publishing, Physics in Medicine and Biology, 2004, vol. 49, pp. 5489-5503.
Taylor et al., Molecular subgroups of medulloblastoma: the current consensus, Consensus Paper, Acta Neuropathol, 2012, vol. 123, pp. 465-472.
Thavavel et al., Regularized Computed Tomography using Complex Wavelets, International Journal of Magnetic Resonance Imaging, 2007, vol. 01, No. 01, pp. 027-032.
Thielen et al., Ultrafast dynamic computed tomography myelography for the precise identification of high-flow cerebrospinal fluid leaks caused by spiculated spinal osteophytes, J Neurosurg Spine, Clinical Article, Mar. 2015, vol. 22, pp. 324-331.
Spaide et al., Retinal Vascular Layers Imaged by Fluorescein Angiography and Optical Coherence Tomography Angiography, Original investigation, JAMA Opthalmology, Jan. 2015, vol. 133, No. 1, pp. 45-50.
Ren et al., Phase-resolved functional optical coherence tomography: simultaneous imaging of in situ tissue structure, blood flow velocity, standard deviation, birefirngence, and Stokes vectors in human skin, Optics Letters, Oct. 1, 2002, vol. 27, No. 19, pp. 1702-1704.
Shenoi, Introduction to Digital Signal Processing and Filter Design, Wiley, 2006, Chapters 3-5 (217 pages).
Srinivasan et al., Quantitative Cerebral Blood Flow with Optical Coherence Tomography, Optics Express, Feb. 1, 2010, vol. 18, No. 3, pp. 2477-2494.
Steane, An introduction to spinors, Dec. 13, 2013, pp. 1-23 (Cornell University Archive, arXiv No. 1312.3824v1).
Thompson et al., Prognostic Value of Medulloblastoma Extent of Resection After Accounting for Molecular Subgroup: A Retrospective Integrated Clinical and Molecular Analysis, Lancet Oncol. Apr. 2016, vol. 17, No. 4, pp. 484-495.
Timmons, Image-Guided Neurosurgery: Integration of Medical Image Data with a Real-time View of the Surgical Field, Jun. 1997, pp. 1-66.
Tran et al., Learning Spatiotemporal Features with 3D Convolutional Networks, Proceedings of the 2015 IEEE International Conference on Computer Vision (ICCV), (2015) pp. 4489-4497.
Rao et al., Shear strain imaging using shear deformations (2008) Med. Phys. 35(2):412-423.
Weaver et al., Brain mechanical property measurement using MRE with intrinsic activation Phys. Med. Biol. (2012) 57:7275-7287.
Kashif et al., Model-Based Noninvasive Estimation of Intracranial Pressure from Cerebral Blood Flow Velocity and Arterial Pressure, Sci. Transl. Med. (2012) vol. 4, No. 129, pp. 1-10.
Bayer et al., Two-Dimensional Simulations of Displacement Accumulation Incorporating Shear Stain, Ultrason. Imaging (2014) vol. 36(1):55-73.
Feingold et al., Quantitative volumetric perfusion mapping of the microvasculature using contrast ultrasound, Invest Radiol. (2010) 45:669-674.
Johnson et al., Local mechanical properties of white matter structures in the human brain, NeuroImage (2013) 79:145-152.
Khullar et al., Wavelet-based fMRI analysis: 3-D denoising, signal seperation, and validation metrics, NeuroImage (2011) 54:2867-2884.
Lee et al., Wavelet Methods for Inverting the Radon Transform with Noisy Data, IEEE Transactions on Image Processing, (2001) vol. 10, No. 1, pp. 79-94 (16 pages) (https://www.math.purdue.edu/~lucier/692/tomography.pdf).
Kutyniok et al., ShearLab 3D: Faithful Digital Shearlet Transforms based on Compactly Supported Shearlets, (2014) (39 pages) (Cornell University Archive, arXiv No. 1402.5670v1).
R-Forge User's Manual, (2011), SVN Revision: 227, 10 pages.
Daubechies Ten Lectures of Wavelets, Springer-Verlag, (1992), from CBMS-NSF Regional Conference Series in Applied Mathematics Society for Industrial and Applied Mathematics 1990 (344 pages).
Lawton, Seven Aneurysms Tenets and Techniques for Clipping (2011) Section 1, Thieme Medical Publishers, New York, Section 1, (36 pages).
Zhao et al., Ultrasound Contrast Imaging Based on a Novel Algorithm Combined Pulse Inversion with Wavelet Transform, Ultrasound in Medicine & Biology, 2011, vol. 37, No. 8, pp. 1292-1305.
Faubel et al., Cilia-based flow network in the brain ventricles, Neurophysiology, Jul. 8, 2016, vol. 353, iss. 6295, pp. 176-178.
Marshall et al., Cilia orientation and the fluid mechanics of development, Current Opinion in Cell Biology, 2008, vol. 20(1), pp. 48-52.
Ohata et al., Mechanosensory Genes Pkd1 and Pkd2 Contribute to the Planar Polarization of Brain Ventricular Epithelium, The Journal of Neuroscience, Aug. 5, 2015, vol. 35(31), pp. 11153-11168.
Jalalvand et al., Ciliated neurons lining the central canal sense both fluid movement and pH through ASIC3, Nature Communications, Jan. 8, 2016, pp. 1-12.
Wagshul et al., Resonant and notch behavior in intracranial pressure dynamics, J Neurosurgery Pediatrics, May 2009, vol. 3(5), pp. 354-364.
Park et al., Alterations of pulsation absorber characteristics in experimental hydrocephalus, J Neurosurg Pediatrics, Aug. 2010, vol. 6(2), pp. 159-170.
Kotelnikov, On the transmission capacity of the "ether" and of cables in electrical communication, Proceedings of the first All-Union Conference on the technological reconstruction of the communications sector and low-current engineering, Moscow 1933, vol. 1, pp. 1-23.
Sagel et al., Gated computed tomography of the human heart, Investigative radiology, Nov.-Dec. 1977, vol. 12, iss. 6, pp. 563-566.
Sarode et al., Video Motion Magnification Using Spatio-Temporal Algorithm, International Journal of Computer Applications (0975-8887), Jun. 2014, vol. 96, No. 9, pp. 9-13.

(56) References Cited

OTHER PUBLICATIONS

Zhao et al., Phase-Resolved Optical Coherence Tomography and Optical Doppler Tomography for Imaging Blood Flow in Human Skin with Fast Scanning Speed and High Velocity Sensitivity, Optics Letters, Jan. 15, 2000, vol. 25, iss. 2, pp. 114-116.

Wu et al., Eulerian Video Magnification for Revealing Subtle Changes in the World, ACM Transactions on Graphics, Jul. 1, 2012, vol. 31, iss. 4, pp. 1-8.

Wang et al., Phase-Sensitive Optical Coherence Elastography for Mapping Tissue Microstains in Real Time, Applied Physics Letter, 2007, vol. 90, pp. 164105-1-164105-3.

Robles et al., Assessing Hemoglobin Concentration Using Spectroscopic Optical Coherence Tomography for Feasibility of Tissue Diagnostics, Biomedical Optics Express, Aug. 2, 2010, vol. 1, No. 1, pp. 310-317.

Lahiri et al., Medical Applications of Infrared Thermography: A Review, Infrared Physics & Technology, 2012, vol. 55, pp. 221-235.

Mourant et al., Hemoglobin Parameters from Diffuse Reflectance Data, Journal of Biomedical Optics, Mar. 2014, vol. 19, iss. 3, pp. 037004-1-037004-9.

Makita et al., Optical Coherence Angiography, Optics Express, Aug. 21, 2006, vol. 14, No. 17, pp. 7821-7840.

Chen et al., Noninvasive Imaging of in vivo blood flow velocity using optical Doppler tomography, Optics Letters, Jul. 15, 1997, vol. 22, No. 14, pp. 1119-1121.

Izatt et al., In vivo bidirectional color Doppler flow imaging of picoliter blood volumes using optical coherence tomography, Optics Letters, Sep. 15, 1997, vol. 22, No. 18, pp. 1439-1441.

Drexler, Ultrahigh-Resolution Optical Coherence Tomography, Journal of Biomedical Optics, Jan./Feb. 2004, vol. 9, iss. 1, pp. 47-74.

Devor et al., Frontiers in optical imaging of cerebral blood flow and metabolism, Journal of Cerebral Blood Flow & Metabolism, 2012, vol. 32, pp. 1259-1276.

Chen et al., Optical Doppler Tomography, IEEE Journal on Selected Topics in Quantum Electronics, Jul. 1, 1999, vol. 5, No. 4, pp. 1134-1142.

Bachmann et al., Fluorescence Spectroscopy of Biological Tissues—A Review, Applied Spectroscopy Reviews, 2006, vol. 41, pp. 575-590.

Desmettre et al., Fluorescence Properties and Metabolic Features of Indocyanine Green (ICG) as Related to Angiography, Survey of Ophthalmology, Jul.-Aug. 2000, vol. 45, No. 1, pp. 15-27.

Martin et al., Hydrodynamic and longitudinal impedance analysis of cerebrospinal fluid dynamics at the craniovertebral junction in type I Chiari malformation, PloS One, Oct. 2013, vol. 8, iss. 10, pp. 1-9.

Candes et al., New Tight Frames of Curvelets and Optimal Representations of Objects with C2 Singularities, Nov. 2002, pp. 1-39 (http://citeseerx.ist.psu.edu/viewdoc/download?doi=10.1.1.162.1548&rep=rep 1&type=pdf).

Cense et al., Ultrahigh-resolution high-speed retinal imaging using spectral-domain optical coherence tomography, Optics Express, May 31, 2004, vol. 12, No. 11, pp. 2435-2447 (13 pages).

Cheng et al., Mammalian DNA Methyltransferases: A Structural Perspective, Structure, Review, Mar. 2008, vol. 16, No. 3, pp. 341-350.

Coumans et al., Volumetric analysis of syringomyelia following hindbrain decompression for Chiari malformation Type I : syringomyelia resolution follows exponential kinetics, Neurosurg Focus, Sep. 2011, vol. 31, No. 3:E4, pp. 1-4.

Dahmen, Wavelet and Multiscale Methods for Operator Equations, 1997 (146 pages).

Deutsch et al., Information Flow in Entangled Quantum Systems, (1999) pp. 1-24 (https://arxiv.org/ftp/quant-ph/papers/9906/9906007.pdf).

Donoho, Compressed Sensing, Sep. 14, 2004, pp. 1-34.

Donoho et al., Message-Passing Algorithms for Compressed Sensing, PNAS, Nov. 10, 2009, vol. 106, No. 45, pp. 18914-18919.

Duverger et al., Concentrations of Putative Neurovascular Transmitters in Major Cerebral Arteries and Small Pial Vessels of Various Species, Journal of Cerebral Blood Flow and Metabolism, 1987, vol. 7, No. 4, pp. 497-501.

Eastwood, The Penrose Transform for Complex Projective Space, Cornell University Archive, Aug. 17, 2008, pp. 1-11 (https://arxiv.org/abs/0808.2321, arXiv:0808.2321v1).

Eastwood et al., Cohomology and Massless Fields, Commun. Math. Phys. (1981) vol. 78, pp. 305-351.

Edelman et al., Nitric Oxide: Linking Space and Time in the Brain, Proc. Natl. Acad. Sci. USA, Dec. 1992, vol. 89, pp. 11651-11652.

Feichtinger et al., Gabor Frames and Time-Frequency Analysis of Distributions, Journal of Functional Analysis, 1997, vol. 146, No. FU963078, pp. 464-495.

Feng et al., Conservation and Divergence of Methylation Patterning in Plants and Animals, PNAS, May 11, 2010, vol. 107, No. 19, pp. 8689-8694.

Fisher et al., Group Formation, Relatedness, and the Evolution of Multicellularity, Current Biology, Jun. 17, 2013, vol. 23, No. 12, pp. 1120-1125.

Fujimoto et al., Optical Coherence Tomography: An Emerging Technology for Biomedical Imaging and Optical Biopsy, Neoplasia, Jan.-Apr. 2000, vol. 2, Nos. 1-2, pp. 9-25.

Goriely et al., Mechanics of the brain: perspectives, challenges, and opportunities, Biomech Model Mechanobiol, 2015, vol. 14, pp. 931-965.

Guerquin-Kern et al., A Fast Wavelet-Based Reconstruction Method for Magnetic Resonance Imaging, IEEE Transactions on Medical Imaging, Institute of Electrical and Electronics Engineers, 2011, 14 pages (obtained from HAL archives-ouvertes).

Guo et al., Sparse Multidimensional Representations using Anisotropic Dilation and Shear Operators, 2005, 13 pages (https://www.math.uh.edu/~dlabate/Athens.pdf).

Han, Properties of Discrete Framelet Transforms, Math. Model. Nat. Phenom., 2013, vol. 8, No. 1, pp. 18-47 (32 pages).

Heil, What is a Frame?, Notices of the AMS, 2013, vol. 60, No. 6, pp. 748-750.

Herz et al., Ultrahigh resolution optical biopsy with endoscopic optical coherence tomography, Optics Express, Jul. 26, 2004, vol. 12, No. 15, pp. 3532-3542.

Hogeweg, Cellular Automata as a Paradigm for Ecological Modeling, Applied Mathematics and Computation, 1988, vol. 27, pp. 81-100.

Hormander, The Spectral Function of an Elliptic Operator, Acta Math, May 7, 1968, vol. 121, pp. 193-218.

Huff et al., Dnmt1-Independent CG Methylation Contributes to Nucleosome Positioning in Diverse Eukaryotes, Cell, Mar. 13, 2014, vol. 156, No. 6, pp. 1286-1297.

Januszewski et al., Flow-based evalution of cerebral revascularization using near-infrared indocyanine green videoangiography, Neurosurg Focus, Feb. 2014, vol. 36, No. 2: E14, pp. 1-8.

Jia et al., Quantitative OCT angiography of optic nerve head blood flow, Biomedical Optics Express, Dec. 1, 2012, vol. 3, No. 12, pp. 3127-3137.

Kamble et al., A Review: Eulerian Video Motion Magnification, International Journal of Innovative Research in Computer and Communication Engineering, Mar. 2015, vol. 3, iss. 3, pp. 2384-2390.

Kim et al., Epigenetic mechanisms in mammals, Cellular and Molecular Life Sciences, 2009, vol. 66, pp. 596-612.

Kittipoom et al., Construction of Compactly Supported Shearlet Frames, Cornell University Archive, 2010, pp. 1-37 (https://arxiv.org/abs/1003.5481, arXiv:1003.5481v2).

Klimenko et al., A cross-correlation technique in wavelet domain for detection of stochastic gravitational waves, 2002, pp. 1-15 (https://arxiv.org/abs/gr-qc/0208007, arXiv:gr-qc/0208007v1).

Knopfmacher et al., Graphs, partitions and Fibonacci numbers, Discrete Applied Mathematics, 2007, vol. 155, pp. 1175-1187.

Koenig et al., Regression of Subependymal Giant Cell Astrocytoma With Rapamycin in Tuberous Sclerosis Complex, J Child Neurol., Oct. 2008, vol. 23, No. 10, pp. 1238-1239.

Kramer et al., Intraventricular fibrinolysis with tissue plasminogen activator is associated with transient cerebrospinal fluid inflamma-

(56) References Cited

OTHER PUBLICATIONS tion: a randomized controlled trial, Journal of Cerebral Blood Flow & Metabolism, 2015, vol. 35, pp. 1241-1248.
Kutyniok et al., Resolution of the Wavefront Set using Continuous Shearlets, Transactions of the American Mathematical Society, May 2009, vol. 361, No. 5, pp. 2719-2754.
Kutyniok et al., Image Separation using Wavelets and Shearlets, International Conference on Curves and Surfaces, 2010, pp. 1-14 (https://www.math.tu-berlin.de/fileadmin/i26_fg-kutyniok/Kutyniok/Papers/ImageSeparation.pdf).
Lee, Wavelet-Vaguelette Decompositions and Homogeneous Equations, Dec. 1997, Purdue University, In Partial Fulfillment of the Requirements for the Degree of Doctor of Philosophy, 103 pages.
Lindenmayer, Developmental Algorithms for Multicellular Organisms: A Survey of L-Systems, J. Theor. Biol., 1975, vol. 54, pp. 3-22.
Lopez et al., The Cauchy problem for a forced harmonic oscillator, Revista Mexicana De Fisica, Dec. 2009, vol. 55, No. 2, pp. 196-215.
Luney et al., Acute Posterior Cranial Fossa Hemorrhage—Is Surgical Decompression Better than Expectant Medical Management?, Neurocritical Care, Apr. 12, 2016, 6 pages.
Gabor, Theory of Communication, Part 3: Frequency Compression and Expansion, 1946, vol. 93, No. 26, pp. 445-457.
Havla et al., Wavelet-based calculation of cerebral angiographic data from time-resolved CT perfusion acquisitions, Eur Radiol. Aug. 2015, vol. 25, No. 8, pp. 2354-2361 (published online Feb. 26, 2015) (8 pages).
Kamp et al., Microscope-Integrated Quantitative Analysis of Intraoperative Indocyanine Green Fluorescence Angiography for Blood Flow Assessment: First Experience in 30 Patients, Operative Neurosurgery 1, vol. 70, Mar. 2012, pp. ons65-ons74.
Mazzola et al., Pediatric Hydrocephalus: systematic literature review and evidence-based guidelines. Part 2: Management of posthemorrhagic hydrocephalus in premature infants, Nov. 2014, J Neurosurg Pediatrics (Suppl), vol. 14, pp. 8-23.
Mccrory et al., Consensus statement on concussion in sport: the 4th International Conference on Concussion in Sport held in Zurich, Nov. 2012, Br J Sports Med, (2013), vol. 47, pp. 250-258.
Michod et al., Cooperation and Conflict in the Evolution of Multicellularity, 2001, The Genetics Society of Great Britain, Heredity, vol. 86, pp. 1-7.
Nehra et al., Peyronie's Disease: AUA Guideline, American Urological Association (AUA) Guideline, approved Apr. 2015, pp. 1-41.
Martin J. Murphy, "Tracking Moving Organs in Real Time", Seminars in Radiation Oncology, vol. 14, No. 1, Jan. 2004, pp. 91-100.
Zhang et al., "Application of Wavelet Thresholding De-noising in DSA," International Symposium on Information Science and Engineering IEEE Computer Society, 2008, pp. 130-134.
Akram et al., "Blood Vessel Enhancement and Segmentation Using Wavelet Transform, International Conference on Digital Image Processing IEEE Computer Society," 2009, pp. 34-38.
Cao et al., "Joint Spatio-Temporal Registration and Microvasculature Segmentation of Retinal Angiogram Sequences," 33rd Annual International Conference of the IEEE EMBS, 2011, pp. 2618-2621.
Tsai et al., "Motion Estimation and Wavelet Transform in Angiogram Video Coding," IEEE, 1994, pp. 1121-1125.
Oh et al., "Reversible Wavelet Compression For Digital Angiograms," Proceedings of the 20th Annual International Conference of the IEEE Engineering in Medicine and Biology Society, 1998, vol. 20, No. 3, pp. 1442-1445.
Tache et al., "Enhanced Visualization of Cerebral Blood Vessels for X-ray Angiograms," IEEE International Conference on E-Health and Bioengineering, 2013, pp. 1-13.
Sun et al., "Morphological enhancement of vascular angiogram with multiscale detected by Gabor filters," Electronics Letters, 2008, vol. 44, No. 2, pp. 1-3.
Munteanu et al., "Wavelet-Based Lossless Compression of Coronary Angiographic Images," IEEE Transactions on Medical Imaging, 1999, vol. 18, No. 3, pp. 272-281.
Lin et al., "Extraction of Coronary Arterial Tree Using Cine X-Ray Angiograms," Biomedical Engineering-Applications, Basis & Communications, 2005, pp. 111-120.
Hohne et al., "Fourier Domain Techniques for Digital Angiography of the Heart," IEEE Transactions on Medical Imaging, 1984, vol. MI-3, No. 2, pp. 62-67.
Hohne et al., "Proceedings of SPIE: Digital Angiography of The Heart In The Frequency Domain," Medical Images and Icons IEEE, 1984, pp. 245-250.
Havla et al., "Validation of a method to differentiate arterial and venous vessels in CT perfusion data using linear combinations of quantitative time-density curve characteristics," Eur. Radiol., 2015, vol. 25, pp. 2937-2944.
Farge, M., "Wavelet Transforms and Their Applications to Turbulence," Annu. Rev. Fluid Mech., 1992, vol. 24, pp. 395-457.
Havla, et al., "Classification of arterial and venous cerebral vasculature based on wavelet postprocessing of CT perfusion data," Med. Phys. (2016) 43 (2), pp. 702-709.
Wendy Bottinor, MD, et al. "Adverse Reactions to Iodinated Contrast Media", International Journal of Angiology, vol. 22, No. 3/2013, Aug. 16, 2013, 5 pages.
Yumi Yanaga, et al., "Contrast Material Injection Protocol With the Dose Adjusted to the Body Surface Area for MDCT Aortography", AJR:194, Apr. 2010, 6 pages.
Keika Ose, et al., "'Gadolinium' as an Alternative to Iodinated Contrast Media for X-Ray Angiography in Patients With Severe Allergy", Circ J 2005; 69: 507-509, Circulation Journal, vol. 69, Apr. 2005, 3 pages.
H. Kälsch, M.D., et al., "Gadolinium-Based Coronary Angiography in Patients with Contraindication for Iodinated X-Ray Contrast Medium: A Word of Caution", Journal of Interventional Cardiology, vol. 21, No. 2, 2008, 9 pages.
Rohit S. Loomba, MD, et al., "Comparison of Contrast Volume, Radiation Dose, Fluoroscopy Time, and Procedure Time in Previously Published Studies of Rotational Versus Conventional Coronary Angiography", The American Journal of Cardiology, Am J Cardiol 2015;116:43e49, 7 pages.
Hrvoje Lusic, et al., "X-Ray Computed Tomography Contrast Agents", Chem Rev. Mar. 13, 2013; 113(3), NIH-PA Author Manuscript, 64 pages.
Kreton Mavromatis, MD, "The Imperative of Reducing Contrast Dose in Percutaneous Coronary Intervention", Editorial Comment, JACC: Cardiovascular Interventions, vol. 7, No. 11, 2014, 3 pages.
Sun Y. Lee, et al., "A Review: Radiographic Iodinated Contrast Media-Induced Thyroid Dysfunction", J Clin Endocrinol Metab., Feb. 2015; 100(2): 376-383, Published online Nov. 6, 2014, 15 pages.
Medda et al., A wavelet clustering technique for the identification of functionally connected regions in the rat brain using resting state fMRI, IEEE Statistical Signal Processing Workshop (SSP), Aug. 2012, pp. 424-427.
Mizuno-Matsumoto et al., Wavelet-crosscorrelation analysis: Nonstationary analysis of neurophysiological signals, Brain Topography, 2005, vol. 17, No. 4, pp. 237-252.
Morlet et al, Wave propagation and sampling theory-part I: Complex signal and scattering in multilayered media, Geophysics, Feb. 1982, vol. 47, No. 2, pp. 203-221.
Najmi et al., The continuous wavelet transform and variable resolution time-frequency analysis, Johns Hopkins Apl Technical Digest, 1997, vol. 18, No. 1, pp. 134-140.
Schultze-Kraft et al., Exploiting the potential of three dimensional spatial wavelet analysis to explore nesting of temporal oscillations and spatial variance in simulateous EEG-fMRI data, Progress in Biophysics and Molecular Biology, Mar. 2011, vol. 105(1-2), pp. 67-79.
Serroukh, Wavelet coefficients cross-correlation analysis of times series, Electronic Journal of Applied Statistical Analysis, 2012, vol. 5, iss. 2, pp. 289-296.
Shannon, Communication in the Presence of Noise, Proceedings of the IEEE, Feb. 1998, vol. 86, iss. 2, pp. 447-457.

(56) References Cited

OTHER PUBLICATIONS

Hardesty et al., Safety, efficacy, and cost of intraoperative indocyanine green angiography compared to intraoperative catheter angiography in cerebral aneurysm surgery, Journal of clinical neuroscience, Apr. 2014, pp. 1-6.
Hyvarinen et al., Indocyanine green fluorescence angiography, Acta Ophthalmologica, Aug. 1980, vol. 58(4), pp. 528-538.
Aaslid et al., Noninvasive transcranial doppler ultrasound recording of flow velocity in basal cerebral arteries, J Neurosurg, 1982, vol. 57(6), pp. 769-774.
Vo et al., Vonn distribution of relative phase for statistical image modeling in complex wavelet domain, Signal Processing, 2011, vol. 91(1), pp. 114-125.
Abramovich et al., Wavelet Analysis and Its Statistical Applications, Journal of the Royal Statistical Society Series D (The Statistician), 2000, vol. 49(1), pp. 1-29.
Kim et al., Cine MR CSF flow study in hydrocephalus: what are the valuable parameters? Acta neurochirurgica Supplement, 1998, vol. 71(6), pp. 343-346.
Kulkarni et al., Endoscopic third ventriculostomy in the treatment of childhood hydrocephalus, The Journal of Pediatrics, Aug. 2009, vol. 155, No. 2, pp. 254-259.
Meairs et al., Ultrasound, microbubbles and the blood-brain barrier, Progress in Biophysics & Molecular Biology, Apr. 2007, vol. 93(1-3), pp. 354-362.
Saikali et al., A three-dimensional digital segmented and deformable brain atlas of the domestic pig, Journal of Neuroscience Methods, Sep. 2010, vol. 192(1), pp. 102-109.
Wilson, Monro-Kellie 2.0: The dynamic vascular and venous pathophysiological components of intracranial pressure, Journal of Cerebral Blood Flow & Metabolism, May 2016, vol. 36(8), pp. 1338-1350.
Bernstein et al., Handbook of MRI Pulse Sequences, Elsevier Academic Press, 2004, pp. 443-454.
Kim et al., Phase-shift between arterial flow and ICP pulse during infusion test, Acta Neurochirurgica, Feb. 3, 2015, vol. 157(4), pp. 633-638.
Kawoos et al., Advances in Intracranial Pressure Monitoring and Its Significance in Managing Traumatic Brain Injury, International Journal of Molecular Sciences, 2015, vol. 16 (12), pp. 28979-28997.
Gabor, Theory of communication. Part 2: The analysis of hearing, Journal of the Institution of Electrical Engineers—Part III: Radio and Communication Engineering, 1946, vol. 93(26), pp. 442-445.
Goriely et al., Mechanics of the brain: perspectives, challenges, and opportunities, Biomechanics and modeling in mechanobiology, Feb. 26, 2015, vol. 14(5), pp. 931-965.
Helbok et al., Intracranial Pressure and Cerebral Perfusion Pressure Monitoring in Non-TBI Patients: Special Considerations, Neurocritical Care, 2014, vol. 21(S2), pp. S85-S94 (published online, Sep. 11, 2014, 10 pages).
Balestreri et al., Intracranial hypertension: what additional information can be derived from ICP waveform after head injury?, Acta Neurochirurgica (wien), 2004, vol. 146(2), pp. 131-141.
Carrera et al., What Shapes Pulse Amplitude of Intracranial Pressure?, Journal of Neurotrauma, Feb. 2010, vol. 27(2), pp. 317-324.
Bangare et al., Reviewing Otsu's method for image thresholding, International Journal of Applied Engineering Research, 2015, vol. 10, No. 9, pp. 21777-21783.
Bhadelia et al., Analysis of cerebrospinal fluid flow waveforms with gated phase-contrast MR velocity measurements, American Journal of Neuroradiology, Feb. 1995, vol. 16(2), pp. 389-400.
Bonnefous et al., Quantification of arterial flow using digital subtraction angiography, Medical Physics, Oct. 2012, vol. 39, iss. 10, pp. 6264-6275.
Chang et al., Emerging techniques for evaluation of the hemodynamics of intracranial vascular pathology, The Neuroradiology Journal, Feb. 2015, vol. 28(1), pp. 19-27.
Dawkins et al., Complications of cerebral angiography: A prospective analysis of 2,924 consecutive procedures, Neuroradiology, Aug. 2007, vol. 49, iss. 9, pp. 753-759.
Torrence et al., A Practical Guide to Wavelet Analysis, Bulletin of the American Meteorological Society, Jan. 1998, vol. 79, iss. 1, pp. 61-78.
Zou et al., Increased Phase Synchronization between Intracranial Pressure and Arterial Blood Pressure during Elevated Intracranial Pressure in Dogs, Proceedings of the 2005 IEEE, Engineering in Medicine and Biology 27th Annual Conference, Shanghai, China, Sep. 1-4, 2005, pp. 315-318.
Unekawa et al., RBC velocities in single capillaries of mouse and rat brains are the same, despite 10-fold difference in body size, Brain Research, 2010, vol. 1320, pp. 69-73.
Grinsted et al., Application of the cross wavelet transform and wavelet coherence to geophysical time series, Nonlinear Processes in Geophysics, 2004, vol. 11, pp. 561-566.
Grist et al., Time-Resolved Angiography: Past, Present, and Future, Journal of Magnetic Resonance Imaging, 2012, vol. 36(6), pp. 1273-1286.
Jiang et al., Computational Fluid Dynamics Simulations of Intracranial Aneurysms at Varying Heart Rates: A "Patient-Specific" Study, Journal of Biomechanical Engineering, Sep. 2009, vol. 131(9), pp. 09100-1-09100-11.
Kachelriess et al., ECG-correlated image reconstruction from subsecond multi-slice spiral CT scans of the heart, Medical Physics, 2000, vol. 27(12), pp. 1881-1902.
Kirk et al., Phase-only complex-valued spatial filter, Journal of the Optical Society of America, Aug. 1971, vol. 61, iss. 8, pp. 1023-1028.
Latka et al., Phase dynamics in cerebral autoregulation, American journal of physiology, heart and circulatory physiology, 2005, vol. 289(5), pp. H2272-H2279.
Shpilfoygel et al., X-ray videodensitometric methods for blood flow and velocity measurement: A critical review of literature, Medical Physics, Sep. 2000, vol. 27, iss. 9, pp. 2008-2023.
Mistretta, Sub-Nyquist acquisition and constrained reconstruction in time resolved angiography, Medical Physics, 2011, vol. 38, iss. 6, pp. 2975-2985.
Peng et al., Wavelet phase synchronization analysis of cerebral blood flow autoregulation, IEEE Transactions on Biomedical Engineering, Apr. 2010, vol. 57, No. 4, pp. 960-968.
Pereira et al., A DSA-based method using contrast motion estimation for the assessment of the intra-aneurysmal low changes induced by flow-diverter stents, American Journal of Neuroradiology, Apr. 2013, vol. 34(4), pp. 808-815.
Butler, W.E., "Wavelet brain angiography suggests arteriovenous pulse wave phase locking," PLOS One, vol. 12, No. 11, Nov. 15, 2017 (16 pages).
Hyvarinen, L., et al., "Indocyanine green fluorescence angiography." Acta ophthalmologica, vol. 58, No. 4, pp. 528-538, 1980 (11 pages).
Desmettre, T., et al., "Fluorescence properties and metabolic features of indocyanine green (ICG) as related to angiography," Survey of ophthalmology, vol. 45, No. 1, pp. 15-27, Jul. 2000 (13 pages).
Kuroiwa, T et al., "Development and clinical application of near-infrared surgical microscope: preliminary report," Minimally Invasive Neurosurgery, vol. 44, No. 4, pp. 240-242, 2001. Abstract accessed online on Jun. 16, 2020 at: <http://www.thieme-connect.de/DOI/DOI?10.1055/s-2001-19929> (2 pages).
Mourant, J. et al., "Hemoglobin parameters from diffuse reflectance data," Journal of Biomedical Optics, vol. 19, No. 3, p. 037004, 2014 (10 pages).
Robles, E., et al., "Assessing hemoglobin concentration using spectroscopic optical coherence tomography for feasibility of tissue diagnostics," Biomedical Optics Express, vol. 1, No. 1, p. 310, 2010 (8 pages).
Lahiri, B., et al., "Medical applications of infrared thermography: A review," Infrared Physics & Technology, vol. 55, No. 4, pp. 221-235, Jul. 2012 (16 pages).
Bachmann, L. et al., "Fluorescence Spectroscopy of Biological Tissues: A Review," Applied Spectroscopy Reviews, vol. 41, No. 6, pp. 575-590, Jul. 2006 (16 pages).
Devor, A., et al., "Frontiers in optical imaging of cerebral blood flow and metabolism," Journal of Cerebral Blood Flow and Metabolism, vol. 32, No. 7, pp. 1259-1276, Jan. 18, 2012 (18 pages).

(56) References Cited

OTHER PUBLICATIONS

Chen, Z., et al., "Optical Doppler tomography," IEEE Journal on Selected Topics in Quantum Electronics, vol. 5, No. 4, pp. 1134-1142, Jul. 1, 1999 (10 pages).
Romain Lacroix, "3D Optical flow analysis of a pulsed contrast agent in the bloodstream. Application to virtual angiography and Magnetic Particle Imaging", Medical Imaging, Télécom Bretagne; Université de Bretagne Occidentale, Apr. 5, 2016, English, tel-01298049, https://hal.archives-ouvertes.fr/tel-01298049/document, 48 pages.
Jerome Revaud, et al., "EpicFlow: Edge-Preserving Interpolation of Correspondences for Optical Flow", May 19, 2019, https://arxiv.org/pdf/1501.02565v2.pdf, 11 pages.
Navid Nourani-Vatani, et al., "A Study of Feature Extraction Algorithms for Optical Flow Tracking", Dec. 5, 2012, https://www.araa.asn.au/acra/acra2012/papers/pap105.pdf, 7 pages.
International Search Report and Written Opinion in corresponding International Application No. PCT/US2022/022152, mailed Jun. 27, 2022, 11 pages.
Wikipedia article entitled "Band-pass filter", <https://en.wikipedia.org/wiki/Band-pass_filter>, last edited on Feb. 25, 2020, accessed on Mar. 26, 2020 (4 pages).
YouTube video, "Eulerian Video Magnification" accessed online on Jun. 15, 2020 at: <https://www.youtube.com/watch?v=ONZcjs1Pjmk>, published May 23, 2012 (2 pages).
U.S. Appl. No. 62/824,582 Entitled Device and Method for Reconstructing Cardiac Frequency Phenomena in Angiographic Data, Filed on Mar. 27, 2019 (25 pages).
Bracewell, R. N., "Two-Dimensional Imaging", Prentice Hall, chapters 4-7, 12, and 15, 1995 (pp. 1-100 of 206 pages).
Bracewell, R. N., "Two-Dimensional Imaging", Prentice Hall, chapters 4-7, 12, and 15, 1995 (pp. 101-206 of 206 pages).
Des Plantes, "Eine Neue Methode Zur Differenzierung in der Rontgenographie (Planigraphies)," Acta Radiologica, 13:2, 182-192, 1932 (16 pages).
Tuy, H. K., "An Inversion Formula for Cone-Beam Reconstruction," SIAM Journal on Applied Mathematics, 43(3):546-552, 1983 (7 pages).
Wikipedia article "Dose Area Product" accessed online on Jun. 15, 2020 at: <https://en.wikipedia.org/wiki/Dose_area_product> (2 pages).
Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (8 pages).
Ashmead, John, "Morlet Wavelets in Quantum Mechanics, " Quanta, vol. 1, issue 1, Nov. 2012, pp. 58-70 (13 pages).
Baker et al., "Lucas-Kanade 20 Years On: A Unifying Framework," International Journal of Computer Vision 56(3), 221-255, 2004 (35 pages).
Balakrishnan et al., "VoxelMorph: A Learning Framework for Deformable Medical Image Registration," arXiv:1809.05231 [cs.CV], Sep. 1, 2019 (16 pages).
Bao et al., "Depth-Aware Video Frame Interpolation," IEEE Conference on Computer Vision and Pattern Recognition, pp. 3703-3712, 2019 (10 pages).
Butler, William E., "Wavelet brain angiography suggests arteriovenous pulse wave phase locking," Plos One, Nov. 15, 2017 (23 pages).
Chen et al., "A Labeling-Free Approach to Supervising Deep Neural Networks for Retinal Blood Vessel Segmentation," Chongqing University, China, May 1, 2017 (10 pages).
Bao et al., https://github.com/baowenbo/DAIN, "DAIN (Depth-Aware Video Frame Interpolation)", IEEE Conference on Computer Vision and Pattern Recognition, Long Beach, CVPR 2019 (9 pages).
Dalca et al., "Unsupervised Learning of Probabilistic Diffeomorphic Registration for Images and Surfaces," Jul. 23, 2019 (18 pages).
Garyfallidis et al., "Dipy, a library for the analysis of diffusion MRI data," Frontiers in Neuroinformatics, vol. 8, art. 8, Feb. 21, 2014 (17 pages).
DIPY—Diffusion Imaging In Python; https://dipy.org/; accessed Mar. 1, 2021 (8 pages).
Daubechies, Ingrid, "Ten Lectures on Wavelets," CBMS-NSF Regional Conference Series in Applied Mathematics, Sep. 1992 (342 pages).
Farneback, Gunnar, "Very High Accuracy Velocity Estimation using Orientation Tensors, Parametric Motion, and Simultaneous Segmentation of the Motion Field," Proceedings Eighth IEEE International Conference on Computer Vision, Jul. 2001 (7 pages).
Felsberg and Sommer, "The monogenic signal," IEEE Transactions on Signal Processing, (49), 12, 3136-3144, 2001 (10 pages).
Chapter 2: Multiscale Vessel Enhancement Filtering, pp. 7-16, adapted from: Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (10 pages).
Freeman and Adelson, "The Design and Use of Steerable Filters," IEEE Transactions on Pattern Analysis and Machine Intelligence, vol. 13, No. 9, pp. 891-906, Sep. 1991 (16 pages).
Gabor, D., "Theory of Communication," Sep. 24, 1945 (29 pages).
Goupillaud et al., "Cycle-Octave and Related Transforms in Seismic Signal Analysis," Geoexploration, 23, (1984/85), pp. 85-102 (18 pages).
Harris and Stephens, "A Combined Corner and Edge Detector," Alvey Vision Conference, pp. 147-151, 1988 (5 pages).
Horn and Schunck, "Determining Optical Flow," Artificial Intelligence 17, pp. 185-203, 1981 (19 pages).
Wolfram Research, "ImageDisplacements," Wolfram Language function, https://reference.wolfram.com/language/ref/ImageDisplacements.html, 2016 (5 pages).
Lucas and Kanade, "An Iterative Image Registration Technique with an Application to Stereo Vision," Proceedings DARPA Image Understanding Workshop, Apr. 1981, pp. 121-130 (10 pages).
Morlet et al., "Wave propogation and sampling theory—Part I: Complex signal and scattering in multilayered media," Geophysics, vol. 47, No. 2, Feb. 1982, pp. 203-221 (19 pages).
Shi and Tomasi, "Good Features to Track," IEEE Conference on Computer Vision and Pattern Recognition, Seattle, Jun. 1994 (8 pages).
Simoncelli and Farid, "Steerable Wedge Filters for Local Orientation Analysis," IEEE Transactions on Image Processing, 5(9): 1377-1382, 1996 (10 pages).
Unser and Van De Ville, "Wavelet Steerability and the Higher-Order Riesz Transform," IEEE Transactions On Image Processing, vol. 19, No. 3, Dec. 22, 2009 (17 pages).
Yin et al., "Reducing the X-ray radiation exposure frequency in cardio-angiography via deep-learning based video Interpolation," Jun. 1, 2020 (6 pages).
Anonymous, Artis Zeego, Data Sheet VC21, Multi-axis for interventional imaging, Oct. 2014, 36 pages, www.siemens.com/healthcare.
Babin et al., Segmentation and length measurement of the abdominal blood vessels in 3-D MRI images, Conference Proceedings IEEE Engineering in Medicine and Biology Society, Sep. 2-6, 2009, pp. 4399-4402.
Barfett et al., Intra-vascular blood velocity and volumetric flow rate calculated from dynamic 4D CT angiography using a time of flight technique, The International Journal of Cardiovascular Imaging, Oct. 2014, vol. 30(7), pp. 1383-1392.
Bhadelia et al., Cerebrospinal fluid pulsation amplitude and its quantitative relationship to cerebral blood flow pulsations: a phase-contrast MR flow imaging study, Neuroradiology, Apr. 1997, vol. 39(4), pp. 258-264.
Long et al., Spatiotemporal wavelet analysis for functional MRI, NeuroImage, Oct. 2004, vol. 23(2), pp. 500-516.
Daubechies, The wavelet transform, time-frequency localization, and signal analysis, IEEE Transactions on Information Theory, Sep. 1990, vol. 36, iss. 5, pp. 961-1005.
Gabor, Theory of communication. Part I: The analysis of information, Journal of the Institution of Electrical Engineers—Part III: Radio and Communication Engineering, Nov. 1946, vol. 93(26), pp. 429-441.
Goupillaud et al., Cycle-octave and related transforms in seismic signal analysis, Geoexploration, Oct. 1984, vol. 23, iss. 1, pp. 85-102.

(56) References Cited

OTHER PUBLICATIONS

Kuroiwa et al., Development and clinical application of near-infrared surgical microscope: preliminary report, Minimally invasive neurosurgery: MIN, Dec. 2001, vol. 44(4), pp. 240-242.
Markl et al., 4D Flow MRI, Journal of Magnetic Resonance Imaging (JMRI), Oct. 2012, vol. 36, iss. 5, pp. 1015-1036.
Moser et al., On the accuracy of EPI-based phase contrast velocimetry, Magnetic Resonance Imaging, Nov. 2000, vol. 18, iss. 9, pp. 1115-1123.
Nyquist et al., Certain topics in telegraph transmission theory, Transactions of the American Institute of Electrical Engineers, Feb. 1928, vol. 47, iss. 2, pp. 617-644.
Persson et al., Hydrocephalus prevalence and outcome in a population-based cohort of children born in 1989-1998, Acta Paediatrica, Jun. 2005, vol. 94, iss. 6, pp. 726-732.
Provost et al., 3D Ultrafast ultrasound imaging in vivo, Physics in Medicine and Biology, Sep. 10, 2014, vol. 59, iss. 19, L1-L13.
Raabe et al., Prospective evaluation of surgical microscope-integrated intraoperative near-infrared indocyanine green videoangiography during aneuryism surgery, Journal of Neurosurgery, Dec. 2005, vol. 103, iss. 6, pp. 982-989.
Rao et al., Shear strain imaging using shear deformations, Med Phys., Feb. 2008, vol. 35(2), pp. 412-423.
Rasul et al., Is endoscopic third ventriculostomy superior to shunts in patients with non-communicating hydrocephalus? A systematic review and meta-analysis of the evidence, Acta Neurochirurgica, May 2013, vol. 155, iss. 5, pp. 883-889.
Sugawara et al., Arterial path length measurements required for the pulse wave velocity, Journal of Hypertension, May 2009, vol. 27, iss. 5, pp. 1102-1104.
Tomita et al., Automated method for tracking vast numbers of FITC-labeled RBCs in microvessels of rat brain in vivo using a high-speed confocal microscope system, Microcirculation, Feb. 2008, vol. 15, iss. 2, pp. 163-174.
Unser, Sampling—50 years after Shannon, Proceedings of the IEEE, Apr. 2000, vol. 88, No. 4, pp. 569-587.
Wagshul et al., The pulsating brain: A review of experimental and clinical studies of intracranial pulsatility, Fluids and Barriers of the CNS, Jan. 18, 2011, vol. 8, iss. 5, pp. 1-23.
Weaver et al., Brain mechanical property measurement using MRE with intrinsic activation, Physics in Medicine Biology, Nov. 2012, vol. 57, No. 22, pp. 7275-7287.
Zaidi et al., Indocyanine Green Angiography in the Surgical Management of Cerebral Arteriovenous Malformations: Lessons Learned in 130 Consecutive Cases, Operative Neurosurgery, Jun. 2014, vol. 10, No. 2, pp. 246-251.
Zou et al., Intracranial pressure waves: characterization of a pulsation absorber with notch filter properties using systems analysis, J. Neurosurg Pediatrics, Jul. 2008, vol. 2(1), pp. 83-94.
Henneman et al., Phase analysis of gated myocardial perfusion single-photon emission computed tomography compared with tissue doppler imaging for the assessment of left ventricular dyssynchrony, Journal of the American College of Cardiology, Apr. 2007, vol. 49 (16), pp. 1708-1714.
Kingdom et al., Sensitivity to contrast histogram differences in synthetic wavelet-textures, Vision Research, Mar. 2001, vol. 41(5), pp. 585-598.
Li et al., Cross-frequency coupling during isoflurane anaesthesia as revealed by electroencephalographic harmonic wavelet bicoherence, Neurosciences and Neuroanaesthesia, British Journal of Anaesthesia, Mar. 2013, vol. 110(3), pp. 409-419.
Moore, A modification of the Rayleigh test for vector data, Biometrika, Apr. 1980, vol. 67(1), pp. 175-180.
Mousavi et al., A wavelet transform based method to determine depth of anesthesia to prevent awareness during general anesthesia, Computational and Mathematical Methods in Medicine, 2014, vol. 2014, pp. 1-13.

Rakhmanov et al., A cross-correlation method for burst searches with networks of misaligned gravitational-wave detectors, Institute of Physics Publishing, Classical and Quantum Gravity, Sep. 6, 2005, vol. 22(18), pp. S1311-S1320.
Wang et al., The residual phase estimation of a seismic wavelet using a renyi divergence-based criterion, Journal of Applied Geophysics, Jul. 2014, vol. 106, pp. 96-105.
Yu, Histogram Matching Seismic Wavelet Phase Estimation, May 2012, Masters thesis, University of Houston.
Anor et al., Modeling of blood flow in arterial trees, Focus Article, WIREs Systems Biology and Medicine, Sep./Oct. 2010, vol. 2, pp. 612-623.
Hamberg et al., Quantitative high-resolution measurement of cerebrovascular physiology with slip-ring CT, AJNR Am J Neuroradiol, Apr. 1996, vol. 17(4), pp. 639-650.
Kashif et al., Model-based non-invasive estimation of intracranial pressure from cerebral blood flow velocity and arterial pressure, Science Translational Medicine, Apr. 2012, vol. 4(129): 129ra44.
Lassen et al., Tracer Kinetic Methods in Medical Physiology, 1979, Raven Press, New York.
Linninger et al., A mathematical model of blood, cerebrospinal fluid and brain dynamics, J Mathematical Biology, Dec. 2009, vol. 59(6), pp. 729-759.
Bayer et al., Two-dimensional simulations of displacement accumulation incorporating shear strain, Ultrason Imaging, Jan. 2014, vol. 36(1), pp. 55-73.
Braun et al., High-resolution mechanical imaging of the human brain by three-dimensional multifrequency magnetic resonance elastography at 7T, NeuroImage, Apr. 2014, vol. 90, pp. 308-314.
Feingold et al., Quantitative volumetric perfusion mapping of the microvasculature using contrast ultrasound, Invest Radiol, Oct. 2010, vol. 45(10), pp. 669-674.
Gauthier et al., Assessment of quantitative perfusion parameters by dynamic contrast-enhanced sonography using a deconvolution method, an in vitro and in vivo study, J Ultrasound Med, Apr. 2012, vol. 31(4), pp. 595-608.
Johnson et al., Local mechanical properties of white matter structures in the human brain, NeuroImage, Oct. 2013, vol. 79, pp. 145-152.
Ashmead, Morelet Wavelets in quantum mechanics, Quanta, Nov. 2012, vol. 1, Issue 1, pp. 58-70.
Johnstone et al., Wavelet threshold estimators for data with correlated noise, Journal of the Royal Statistical Society: Series B (Statistical Methodology), 1997, 59(2), pp. 319-351.
Khullar et al., Wavelet-based fMRI analysis: 3-d denoising, signal separation, and validation metrics, NeuroImage, Feb. 2011, vol. 54(4), pp. 2867-2884.
Abdallah, Considerations in perioperative assessment of valproic acid coagulopathy, review article, Journal of Anesthesiology Clinical Pharmacology, Jan.-Mar. 2014, vol. 30, iss. 1, pp. 7-9.
D'Agnolo et al., Radon-Penrose transform for D-modules, Sep. 6, 1994, pp. 1-37.
Penkov, A Geometric Approach to the Linear Penrose Transform, Transactions of the American Mathematical Society, Aug. 1985, vol. 290, No. 2, pp. 555-575.
Wolfram, Statistical mechanics of cellular automata, The American Physical Society, Reviews of Modern Physics, vol. 55, No. 3, Jul. 1983, pp. 601-644.
Sturm et al., New Brain Tumor Entities Emerge from Molecular Classification of CNS-PNETs, Cell, Feb. 25, 2016, vol. 164, iss. 5, pp. 1060-1072.
Liebling et al., Wavelet-based Synchronization of Nongated Confocal Microscopy Data for 4D Imaging of the Embryonic Heart, Proceedings of SPIE 5914, Wavelets XI, 2005, vol. 591409, 6 pages.
Ehrenreich et al., New developments in the understanding of cerebral vasoregulation and vasospasm: the endothelin-nitric oxide network, CME Credit, Cleveland Clinic Journal of Medicine, Mar.-Apr. 1995, vol. 62, No. 2, pp. 105-116.
Vagharshakyan et al., Light Field Reconstruction Using Shearlet Transform, Sep. 29, 2015, pp. 1-12 (Cornell University Archive, https://arxiv.org/abs/1509.08969, arXiv:1509.08969v1).

(56) References Cited

OTHER PUBLICATIONS

Daubechies, Orthonormal Bases of Compactly Supported Wavelets, Communications on Pure and Applied Mathematics, 1988, vol. XLI, pp. 909-996.

Mandelshtam, The Multidimensional Filter Diagonalization Method, Journal of Magnetic Resonance, 2000, vol. 144, pp. 343-356.

Insolera et al., Cortical neurogenesis in the absence of centrioles, Nat Neurosci, Nov. 2014, vol. 17, No. 11, pp. 1528-1536.

Kool et al., Molecular subgroups of medulloblastoma: an international meta-analysis of transcriptome, genetic aberrations, and clinical data of WNT, SHH, Group 3, and Group 4 medulloblastomas, 2012, Acta Neuropathol, vol. 123, pp. 473-484.

Kutyniok et al., Compactly Supported Shearlets, Approximation Theory XIII: San Antonio 2010, pp. 1-24.

Liner, An overview of wavelet transform concepts and applications, University of Houston, Feb. 26, 2010, pp. 1-17.

Liu et al., Motion Magnification, ACM Transactions on Graphics (TOG), Jul. 2005, vol. 24, iss. 3, pp. 519-526 (8 pages).

Lohani et al., Intrasacral meningocele in the pediatric population, J Neurosurg Pediatrics, Jun. 2013, vol. 11, pp. 615-622.

Long et al., Spatiotemporal wavelet analysis for functional MRI, NeuroImage, 2004, vol. 23, pp. 500-516.

Maltz et al., Fixed gantry tomosynthesis system for radiation therapy image guidance based on a multiple source x-ray tube with carbon nanotube cathodes, Medical Physics, May 2009, vol. 36, No. 5, pp. 1624-1636.

Mandelshtam, FDM: the filter diagonalization method for data processing in NMR experiments, Progress in Nuclear Magnetic Resonance Spectroscopy, 2001, vol. 38, pp. 159-196.

Mourant et al., Hemoglobin parameters from diffuse reflectance data, Journal of Biomedical Optics, Mar. 2014, vol. 19, No. 3, pp. 037004-1-037004-9.

D'Ariano, How to Derive the Hilbert-Space Formulation of Quantum Mechanics From Purely Operational Axioms, 20 pages (presented at conference "On the Present Status of Quantum Mechanics" held on Sep. 7-9, 2005, Mali Losinj, Croatia) (Cornell University Archive, https://arxiv.org/abs/quant-ph/0603011, arXiv.quant-ph/0603011v1).

Mixter, Ventriculoscopy and Puncture of the Floor of the Third Ventricle, Boston M. & S. Journal, Mar. 1, 1923, vol. 188, No. 9, pp. 277-278.

Moussa et al., Efficacy of postoperative antibiotic injection in and around ventriculoperitoneal shunt in reduction of shunt infection: A randomized controlled trial, Clinical Neurology and Neurosurgery, 2016, vol. 143, pp. 144-149.

Monici, Cell and tissue autofluorescence research and diagnostic applications, Biotechnology Annual Review, 2005, vol. 11, pp. 227-256.

Drexler et al., In vivo ultrahigh-resolution optical coherence tomography, Optics Letters, Sep. 1, 1999, vol. 24, No. 17, pp. 1221-1223.

Rees et al., Role of endothelium-derived nitric oxide in the regulation of blood pressure, Proc. Natl. Acad. Sci. USA, 1989, vol. 86, pp. 3375-3378.

Rodino et al., The Gabor Wave Front Set (2013) (Cornell University Archive, https://arxiv.org/abs/1207.5628, arXiv:1207.5628v2), pp. 1-29.

Schaer et al., Haptoglobin Preserves Vascular Nitric Oxide Signaling during Hemolysis, American Journal of Respiratory and Critical Care Medicine, May 15, 2016, vol. 193, iss. 10, pp. 1111-1122.

Shumacher, Analog clock and watch reader, 2015, pp. 1-10 (https://www.cs.bgu.ac.il/~ben-shahar/Teaching/Computational-Vision/StudentProjects/ICBV151/ICBV-2015-1-ChemiShumacher/Report.pdf).

Tudor et al., Endoscopic third ventriculostomy (ETV) for idiopathic normal pressure hydrocephalus (iNPH) (Review), Cochran Collection, Cochrane Database of Systematic Reviews, 2015, iss. 7, pp. 1-23.

Khandelwal et al., Age-dependent increase in green autofluorescence of blood erythrocytes, J. Biosci. Sep. 2007, vol. 32, No. 6, pp. 1139-1145.

Wadhwa et al., Phase-Based Video Motion Processing, MIT Computer Science and Artificial Intelligence Lab, ACM Transactions on Graphics, Jul. 2013, vol. 32, No. 4, article 80, pp. 80:1-80:9.

Yang et al., Improved phase-resolved optical Doppler tomography using the Kasai velocity estimator and histogram segmentation, Optics Communications, Jul. 15, 2002, vol. 208, pp. 209-214.

Zhang et al., Orthogonal Complex Filter Banks and Wavelets: Some Properties and Design, IEEE Transactions on Signal Processing, Apr. 1999, vol. 47, No. 4, pp. 1039-1048.

Aaslid et al., Cerebral Autoregulation Dynamics in Humans, Stroke, 1989, vol. 20, pp. 45-52.

Adams et al., Symptomatic Occult Hydrocephalus with "Normal" Cerebrospinal-Fluid Pressure, A Treatable Syndrome, The New England Journal of Medicine, Jul. 15, 1965, vol. 273, No. 3, pp. 117-126.

Barina, Gabor Wavelets in Image Processing, Feb. 10, 2016, 6 pages (Cornell University Archive, https://arxiv.org/pdf/1602.03308.pdf, arXiv:1602.03308v1).

Bernardes et al., Digital Ocular Fundus Imaging: A Review, Ophthalmologica, 2011, vol. 226, pp. 161-181.

Bernardino et al., A Real-Time Gabor Primal Sketch for Visual Attention, Second Iberian Conference on Pattern Recognition and Image Analysis, 2005, 8 pages (http://vislab.isr.ist.utl.pt/publications/05-ibpria-alex.pdf).

Guo et al., Wavelets with composite dilations and their MRA properties, Applied and Computational Harmonic Analysis, 2006, vol. 20, pp. 202-236.

Goh et al., Subependymal giant cell tumors in tuberous sclerosis complex, Neurology, Oct. 2004, vol. 63, pp. 1457-1461.

Bo et al., Symbolic Representations in Motor Sequence Learning, Neuroimage, 2011, vol. 54, No. 1, pp. 417-426.

Bodranghien et al., Consensus Paper: Revisiting the Symptoms and Signs of Cerebellar Syndrome, Cerebellum, Jun. 2016, vol. 15, No. 3, pp. 369-391 (published online Jun. 2015) (23 pages).

Borsdorf et al., Separate CT-Reconstructions for 3D Wavelet Based Noise Reduction Using Correlation Analysis, 2007, IEEE Nuclear Science Symposium Conference Record, pp. 2633-2638.

Brouder et al., A Smooth Introduction to the Wavefront Set, Apr. 7, 2014, pp. 1-29 (Cornell University Archive, https://arxiv.org/pdf/1404.1778.pdf, arXiv:1404.1778v1).

Burt et al., The Laplacian Pyramid as a Compact Image Code, IEEE Transactions on Communications, Apr. 1983, vol. COM-31, No. 4, pp. 532-540.

Forbes et al., Statistical Distributions, Fourth Edition, copyright 2011, John Wiley and Sons, Inc., Chapters 1-9, (84 pages).

Mandelshtam et al., Harmonic inversion of time signals and its applications, AIP The Journal of Chemical Physics 1997, vol. 107, No. 6756, 12 pages.

Schroeder, The Simple Harmonic Oscillator, copyright 2015-2016, 5 pages (https://physics.weber.edu/schroeder/quantum/Harmonic.pdf).

International Standards Organization, ISO/IEC 14496-12 Multimedia Formats Information Technology—Coding of audio-visual objects (2008) 4 pages (Abstract).

Guido et al., Introduction to the special issue on wavelet-based algorithms for medical problems (2007) vol. 37, p. 429.

International Preliminary Report on Patentability for PCT/US2022/022152, issued Nov. 23, 2023 (11 pages).

Office Action in corresponding Japanese Patent Application No. 2023-569838, issued Jun. 7, 2024, with English translation (7 pages).

Yazdanfar, S., et al., "High resolution imaging of in vivo cardiac dynamics using color Doppler optical coherence tomography," Optics Express, vol. 1, No. 13, pp. 424-431, Dec. 22, 1997 (8 pages).

Chen, C., et al., "Optical coherence tomography based angiography [Invited]," Biomedical Optics Express, vol. 8, No. 2. p. 1056, Jan. 24, 2017 (27 pages).

Makita, S., et al., "Optical coherence angiography," Optics Express, vol. 14, No. 17, pp. 114-116, Aug. 21, 2006 (20 pages).

Zhao, Y., et al., "Phase-resolved optical coherence tomography and optical Doppler tomography for imaging blood flow in human skin

(56) References Cited

OTHER PUBLICATIONS with fast scanning speed and high velocity sensitivity," Optics Letters, vol. 25, No. 2, pp. 114-116, Jan. 15, 2000 (4 pages).
Chen, Z., et al., "Noninvasive imaging of in vivo blood flow velocity using optical Doppler tomography," Optics Letters, vol. 22, No. 14, Jul. 15, 1997 (3 pages).
Izatt, J., et al., "In vivo bidirectional color Doppler flow imaging of picoliter blood volumes using optical coherence tomography," Optics Letters, vol. 22, No. 18, Sep. 15, 1997 (3 pages).
Drexler, W., "Ultrahigh-resolution optical coherence tomography," Journal of Biomedical Optics 9(1), 47-74, Jan./Feb. 2004 (28 pages).
Wang, R., et al., "Phase-sensitive optical coherence elastography for mapping tissue microstrains in real time," Applied Physics Letters, vol. 90, No. 16, Apr. 19, 2007 (4 pages).
Wu, H., et al., "Eulerian Video Magnification for Revealing Subtle Changes in the World," Association for Computing Machinery, vol. 31, No. 4, pp. 1-8, Jul. 2012 (9 pages).
Office Action in corresponding Canadian Patent Application No. 3,207,659, issued Nov. 21, 2024 (8 pages).
Gibson, J., et al., "Optical Flow and Trajectory Estimation Methods", SpringerBriefs in Computer Science, vol. 1, pp. 1-49, https://link.springer.com/book/10.1007/978-3-319-44941-8, Sep. 30, 2016 (Sep. 30, 2016) (57 pages).

\* cited by examiner

MOTION-COMPENSATED WAVELET ANGIOGRAPHY

FIELD

The field relates generally to angiography, and in particular, to methods and systems for reconstruction of spatiotemporal images of a moving vascular pulse wave applied to a sequence of angiographic images acquired at faster than cardiac frequency and with large scale motion of vessels, tissues, and/or organs at cardiac frequency.

BACKGROUND

The heart sends blood to the body as a sequence of arterial stroke volumes. When a traveling arterial stroke volume arrives at the vasculature of an organ, the arterial stroke volume induces a coordinated motion of the blood vessels along with an expansion of their diameter to accommodate the passing arterial stroke volume. Since the ventricles of the heart contract at cardiac frequency, these coordinated motions and expansions of arterial blood vessels occur at cardiac frequency throughout the body.

In an angiogram, a bolus of chemical contrast is injected into the vascular system. The contrast allows visualization of blood vessels in the body. Existing techniques are ill-suited for spatiotemporal reconstruction of a moving vascular pulse wave in a vascular object undergoing large-scale motion, such as a blood vessel undergoing large scale motion due to a beating heart. The large-scale motion of the vascular object impedes the measurement of the travel of hemodynamic pulse waves within the object. Such large-scale motion is too great to ignore in an angiogram.

SUMMARY

Embodiments of the invention are directed to methods, systems, and computer readable media for reconstructing cardiac frequency phenomena in angiographic data in which vascular objects (e.g., tissues, organs, vessels, etc.) undergo large-scale motion. These techniques track and compensate for motion in unconstrained vascular objects, and improve existing wavelet angiography techniques in vascular structures undergoing small-scale motion.

Motion in unconstrained vascular objects is referred to herein as large-scale or wide amplitude or unconstrained cardiac frequency motion. The embodiments described herein may be used to track unconstrained cardiac frequency motion of vascular objects, e.g., using an adjusted moving path as a path integral. Embodiments that determine the moving path may be coupled with wavelet or other time-indexing-conserving angiography techniques to allow spatiotemporal reconstruction to be performed on any physiological organ, tissue, or vasculature. This may enable, for example, spatiotemporal reconstruction of a pulse wave at a given point in a blood vessel undergoing large scale motion.

In one form, a method for extracting cardiac frequency angiographic phenomena for an unconstrained vascular object from an angiographic study is provided. The method comprises: obtaining, at a computer, a series of angiographic image frames obtained at a rate faster than cardiac frequency, wherein each image frame comprises a plurality of pixels, and wherein each pixel has a corresponding intensity; applying, at the computer, an optical flow technique to the angiographic image frames to generate a plurality of paths corresponding to a displacement of respective pixels from image frame to image frame; generating, at the computer, a spatiotemporal reconstruction of cardiac frequency angiographic phenomena based on the plurality of paths and the corresponding intensities associated with respective pixels of the paths; and outputting for display the spatiotemporal reconstruction of cardiac frequency angiographic phenomena in one or more images. This method may improve angiographic imaging by compensating for motion in vascular structures.

In one example, the method further comprises: for each image frame, recursively integrating the displacement for a given pixel in a forward temporal direction and in a reverse temporal direction to generate an optical flow trajectory for the given pixel. Recursive integration may enable tracking object motion in vascular structures.

In one example, the method further comprises: selecting an image frame of interest; and determining the displacement for a given pixel of the image frame of interest based on image frames that are within a number of image frames of the image frame of interest. Determining the displacement within a number of image frames may enable maintaining consistency with the frequency resolution of a mother wavelet function. In one example, the number of image frames may be five. The number five may be selected where the heart is beating at a rate of sixty beats per minute and angiographic images are acquired at five Hertz. In this example, determining the displacement within five frames may be equivalent to determining the displacement for one heartbeat before and one heartbeat after the frame of interest. Any suitable number of image frames may be selected, for example, based on the corresponding number of heartbeats before and after the frame of interest (e.g., two heartbeats before and after, half a heartbeat before and after, etc.).

In one example, applying the optical flow technique includes: applying a dense optical flow technique that measures optical flows of the plurality of pixels from image frame to image frame. A dense optical flow technique may enable calculating the displacement of every pixel.

In one example, applying the optical flow technique includes: applying a sparse optical flow technique including: tracking a limited number of object locations from image frame to image frame; and interpolating a movement of intervening object locations. A sparse optical flow technique may enable calculating only the motions of key pixels.

In one example, applying the optical flow technique includes: determining each path based on a local coordinate system. The local coordinate system may reduce computational requirements by simplifying wavelet calculations. The local coordinate system may for example be defined by a particular location in a blood vessel. If the blood vessel is experiencing large scale motion, the vicinity about the particular location that defines the coordinate system may remain well-described by that coordinate system.

In one example, the method further comprises: providing the one or more images as a cine video sequence. The cine video sequence may provide a motion-compensated, wavelet-transformed result.

In another form, a system is provided. The system comprises: a communications interface configured to obtain a series of angiographic image frames obtained at a rate faster than cardiac frequency, wherein each image frame comprises a plurality of pixels, and wherein each pixel has a corresponding intensity; and one or more processors coupled to the communications interface, wherein the one or more processors are configured to: apply an optical flow technique to the angiographic image frames to generate a plurality of paths corresponding to a displacement of respective pixels from image frame to image frame; generate a spatiotemporal reconstruction of cardiac frequency angiographic phenomena based on the plurality of paths and the corresponding intensities associated with respective pixels of the paths; and output for display the spatiotemporal reconstruction of cardiac frequency angiographic phenomena in one or more images. This system may improve angiographic imaging by compensating for motion in vascular structures.

In another form, one or more non-transitory computer readable storage media are provided. The one or more non-transitory computer readable storage media are encoded with instructions that, when executed by a processor, cause the processor to: obtain a series of angiographic image frames obtained at a rate faster than cardiac frequency, wherein each image frame comprises a plurality of pixels, and wherein each pixel has a corresponding intensity; apply an optical flow technique to the angiographic image frames to generate a plurality of paths corresponding to a displacement of respective pixels from image frame to image frame; generate a spatiotemporal reconstruction of cardiac frequency angiographic phenomena based on the plurality of paths and the corresponding intensities associated with respective pixels of the paths; and output for display the spatiotemporal reconstruction of cardiac frequency angiographic phenomena in one or more images. The one or more non-transitory computer readable storage media may improve angiographic imaging by compensating for motion in vascular structures.

Still other objects and advantages of these techniques will be apparent from the specification and drawings.

BRIEF DESCRIPTION OF THE DRAWINGS

FIGS. 4A and 4B are sequential angiogram image frames, with the position of a pixel tracked using the techniques provided herein from frame to frame. FIG. 4C is an overlay of FIG. 4A with FIG. 4B to show displacement of the pixel due to unconstrained vascular motion (e.g., contractility of the heart).

FIG. 6A shows an image before spatiotemporal reconstruction and FIG. 6B shows an image after spatiotemporal reconstruction.

DETAILED DESCRIPTION OF EXAMPLE EMBODIMENTS

Figure 1A:
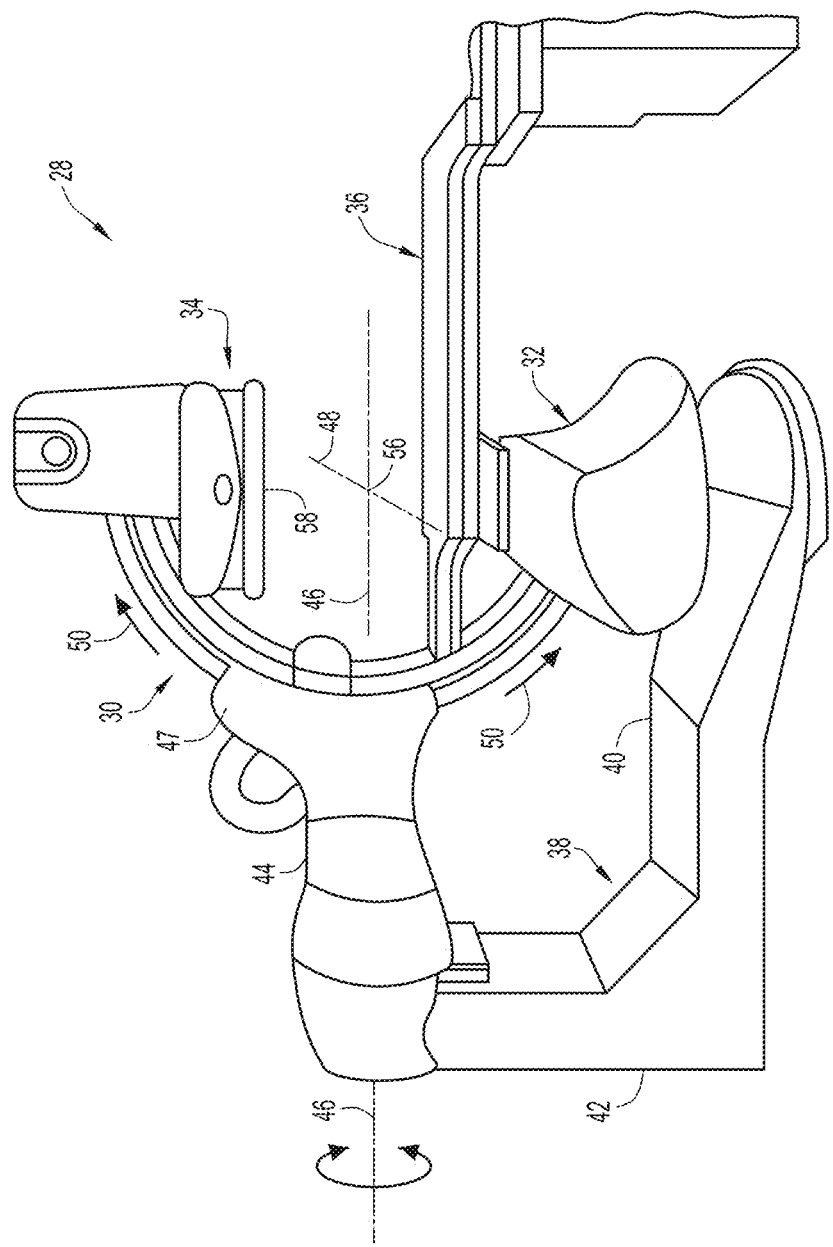
FIGS. 1A and 1B are side and partially schematic views, respectively, showing an example of a rotational x-ray system that may be used with embodiments of the disclosure for acquiring angiographic data.

Present techniques may provide an improvement over existing techniques for angiographic imaging of vessels, tissues and/or organs with unconstrained motion.

For example, existing angiographic techniques are poorly suited for spatiotemporal reconstructions of moving vascular pulse waves through objects with unconstrained vascular motion. For instance, the heart is a muscular organ flanked on its right and left sides by the lungs, which are soft organs without the ability to constrain cardiac motion. Thus, the heart, associated vessels, and tissue are examples of objects that undergo wide amplitude cardiac motion. While existing angiographic techniques may be applied to vessels, tissues and/or organs with wide amplitude cardiac motion, the large-scale motion of such objects presents challenges when trying to measure the travel of hemodynamic pulse waves within the object.

Embodiments of this disclosure may utilize motion tracking for unconstrained vascular objects undergoing motion at cardiac frequency. By tracking the motion of objects in a sequence of two-dimensional images, and using the tracked motion to directionally guide the spatial extent (of the image) encompassed by the wavelet transforms (or other time-indexing-conserving mathematical transforms), spatiotemporal reconstruction may be applied to unconstrained cardiac motion objects.

An angiographic image sequence comprises a set of 2-dimensional image frames acquired at faster than cardiac frequency as a function of time. Thus, this 3-dimensional data set includes two spatial dimensions and one temporal dimension. If there is motion of blood vessels and/or other structures of interest in the angiography image frames, a given location of a given structure will not necessarily occupy the same pixel coordinates in two adjacent or nearby temporal image frames.

According to embodiments of the invention, a pixel may be treated as a time channel, wherein the pixel location may change from frame to frame in a sequence of angiographic images.

Motion tracking is performed on image pixels to allow measurement at cardiac frequency of vascular pulses in a moving heart vessel, tissue, or organ. An image may be processed based on a global coordinate system. The global coordinate system may be represented in angiographic images by a three-dimensional grid. Two dimensions may be defined by horizontal and vertical rows/columns of pixels in an image, and the third dimension may be defined by the image frame number (e.g., the ordinal number of a given image frame in the angiographic image sequence).

Motion may be further tracked with regard to a local coordinate system, e.g., the moving blood vessel, organ, or tissue is tracked with respect to the local coordinate system. For example, each path of an object may be determined based on a local coordinate system. A local coordinate system may be defined for each object or each key pixel in each of the image frames of an angiographic sequence. Suppose an angiogram has a key blood vessel branch point 'a' at frame $t_1$. The spatial coordinates in the two-dimensional image frame of object 'a' are $x_{t1a}$ and $y_{t1a}$. At frame $t_2$, object 'a' has displaced so that its two-dimensional coordinates are $x_{t2a}$ and $y_{t2b}$. In a local coordinate system, object 'a' in image frame $t_1$ may be at position 0 in the x dimension and position 0 in the y dimension. At image frame $t_2$, the displacement of object 'a' may be maintained so that the position of object a remains at 0 in the x dimension and 0 in the y dimension. The portions of the vessel in the neighborhood of object a may be assigned a coordinate location relative to 'a' that remains constant from one image frame to the next.

The local coordinate system may be determined by modifying the global coordinate system based on the motions and displacements of objects. For example, if a particular turn on a blood vessel is measured to move five pixels to the right between one image frame and the next, the flowing blood within that pixel may be treated as having moved the same five pixels in the same direction. In this sense, the blood vessel orients a local coordinate system. In particular, the local coordinate system may be translated five pixels to the right relative to the global coordinate system. Thus, a global coordinate system may serve as a reference coordinate system for one or more local coordinate systems.

Thus, pixels of the image are transformed to the local coordinate system, and a track or path is determined for the transformed pixel to track the position of the pixel over time. This track or path is fed into a wavelet transform or other transform that preserves time indexing. For the purpose of performing the wavelet transform, an angiographic image sequence may be treated as an array of x by y pixels of length t frames (e.g., an x by y array of time signals of length t). A wavelet transform may operate on a one-dimensional sequence of numbers, and thus the techniques described herein may enable tracking the motion of vascular objects if object motion (e.g., the motion within a given pixel) is large relative to the temporal/frequency resolution of the selected mother wavelet (e.g., if the motion is too great to be satisfactory). In particular, the motions of every pixel in every frame may be estimated and the motions may be reversed (e.g., compensated for). The wavelet transform may operate on the motion-reversed data. The motion may be restored in the wavelet transformed data by looking up the motions and applying them. Thus, after the wavelet calculations are complete, the local coordinate systems may be reverted back to the original coordinate system.

Referring to FIGS. 1A-3, exemplary systems or devices that may be employed for carrying out embodiments of the invention are illustrated. It is understood that such systems and devices are only exemplary of representative systems and devices and that other hardware and software configurations are suitable for use with embodiments of the invention. Thus, the embodiments are not intended to be limited to the specific systems and devices illustrated herein, and it is recognized that other suitable systems and devices can be employed without departing from the spirit and scope of the subject matter provided herein.

Figure 1B:
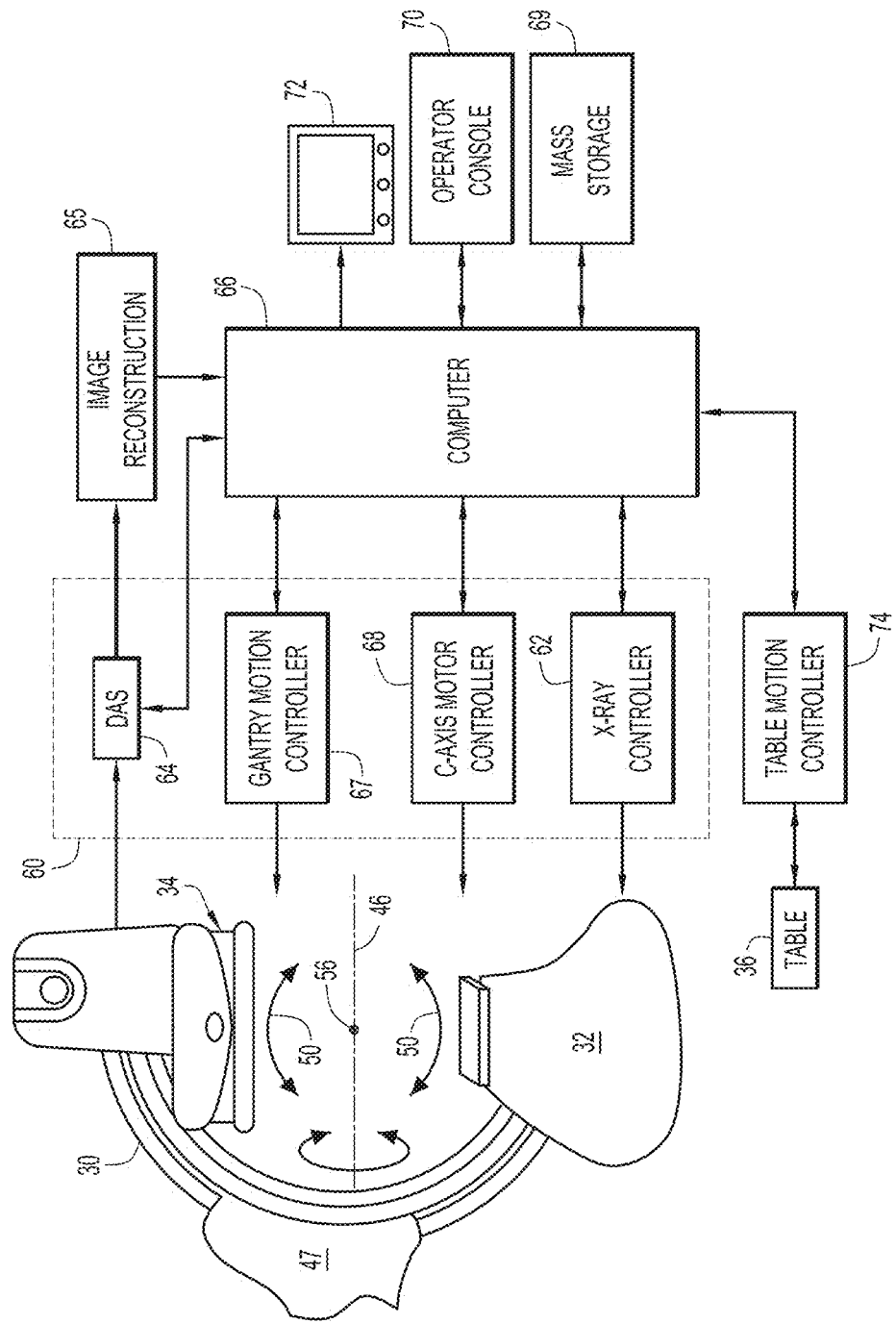

Referring first to FIGS. 1A and 1B, a rotational x-ray system 28 is illustrated that may be employed for obtaining an angiogram at faster than cardiac rate, such as via fluoroscopic angiography. In acquiring an angiogram, a chemical contrast agent may be injected into the patient positioned between an x-ray source and detector, and x-ray projections are captured by the x-ray detector as a two-dimensional image (i.e., an angiographic image frame). A sequence of such image frames comprises an angiographic study, and, in accordance with embodiments of the invention, the angiographic image frames may be acquired at faster than cardiac frequency to allow motion tracking and spatiotemporal reconstruction of the cardiac frequency phenomena into a cardiac space angiogram.

As shown in FIG. 1A, an example of an angiogram imaging system is shown in the form of a rotational x-ray system 28 including a gantry having a C-arm 30 which carries an x-ray source assembly 32 on one of its ends and an x-ray detector array assembly 34 at its other end. The gantry enables the x-ray source assembly 32 and x-ray detector array assembly 34 to be oriented in different positions and angles around a patient disposed on a table 36, while providing to a physician access to the patient. The gantry includes a pedestal 38 which has a horizontal leg 40 that extends beneath the table 36 and a vertical leg 42 that extends upward at the end of the horizontal leg 40 that is spaced apart from table 36. A support arm 44 is rotatably fastened to the upper end of vertical leg 42 for rotation about a horizontal pivot axis 46.

The horizontal pivot axis 46 is aligned with the centerline of the table 36, and the support arm 44 extends radially outward from the horizontal pivot axis 46 to support a C-arm drive assembly 47 on its outer end. The C-arm 30 is slidably fastened to the C-arm drive assembly 47 and is coupled to a drive motor (not shown) which slides the C-arm 30 to revolve about a C-axis 48 as indicated by arrows 50. The horizontal pivot axis 46 and C-axis 48 intersect each other, at a system isocenter 56 located above the table 36, and are perpendicular to each other.

The x-ray source assembly 32 is mounted to one end of the C-arm 30 and the x-ray detector array assembly 34 is mounted to its other end. The x-ray source assembly 32 emits a beam of x-rays which are directed at the x-ray detector array assembly 34. Both assemblies 32 and 34 extend radially inward to the horizontal pivot axis 46 such that the center ray of this beam passes through the system isocenter 56. The center ray of the beam thus can be rotated about the system isocenter around either the horizontal pivot axis 46 or the C-axis 48, or both, during the acquisition of x-ray attenuation data from a subject placed on the table 36.

The x-ray source assembly 32 contains an x-ray source which emits a beam of x-rays when energized. The center ray passes through the system isocenter 56 and impinges on a two-dimensional flat panel digital detector 58 housed in the x-ray detector array assembly 34. The two-dimensional flat panel digital detector 58 may be, for example, a 2048× 2048 element two-dimensional array of detector elements. Each element produces an electrical signal that represents the intensity of an impinging x-ray and hence the attenuation of the x-ray as it passes through the patient. During a scan, the x-ray source assembly 32 and x-ray detector array assembly 34 are rotated about the system isocenter 56 to acquire x-ray attenuation projection data from different angles. In some aspects, the detector array is able to acquire fifty projections, or image frames, per second which is the limiting factor that determines how many image frames can be acquired for a prescribed scan path and speed.

Referring to FIG. 1B, the rotation of the assemblies 32 and 34 and the operation of the x-ray source are governed by a control mechanism 60 of the x-ray system. The control mechanism 60 includes an x-ray controller 62 that provides power and timing signals to the x-ray source assembly 32. A data acquisition system (DAS) 64 in the control mechanism 60 samples data from detector elements and passes the data to an image reconstructor 65. The image reconstructor 65 receives digitized x-ray data from the DAS 64 and performs high speed image reconstruction according to the methods of the present disclosure. The reconstructed image is applied as an input to a computer 66 which stores the image in a mass storage device 69 or processes the image further. Image reconstructor 65 may be a standalone computer or may be integrated with computer 66.

The control mechanism 60 also includes gantry motor controller 67 and a C-axis motor controller 68. In response to motion commands from the computer 66, the motor controllers 67 and 68 provide power to motors in the x-ray system that produce the rotations about horizontal pivot axis 46 and C-axis 48, respectively. The computer 66 also receives commands and scanning parameters from an operator via console 70 that has a keyboard and other manually operable controls. An associated display 72 allows the operator to observe the reconstructed image frames and other data from the computer 66. The operator supplied commands are used by the computer 66 under the direction of stored programs to provide control signals and information to the DAS 64, the x-ray controller 62 and the motor controllers 67 and 68. In addition, computer 66 operates a table motor controller 74 which controls the motorized table 36 to position the patient with respect to the system isocenter 56.

Figure 2:
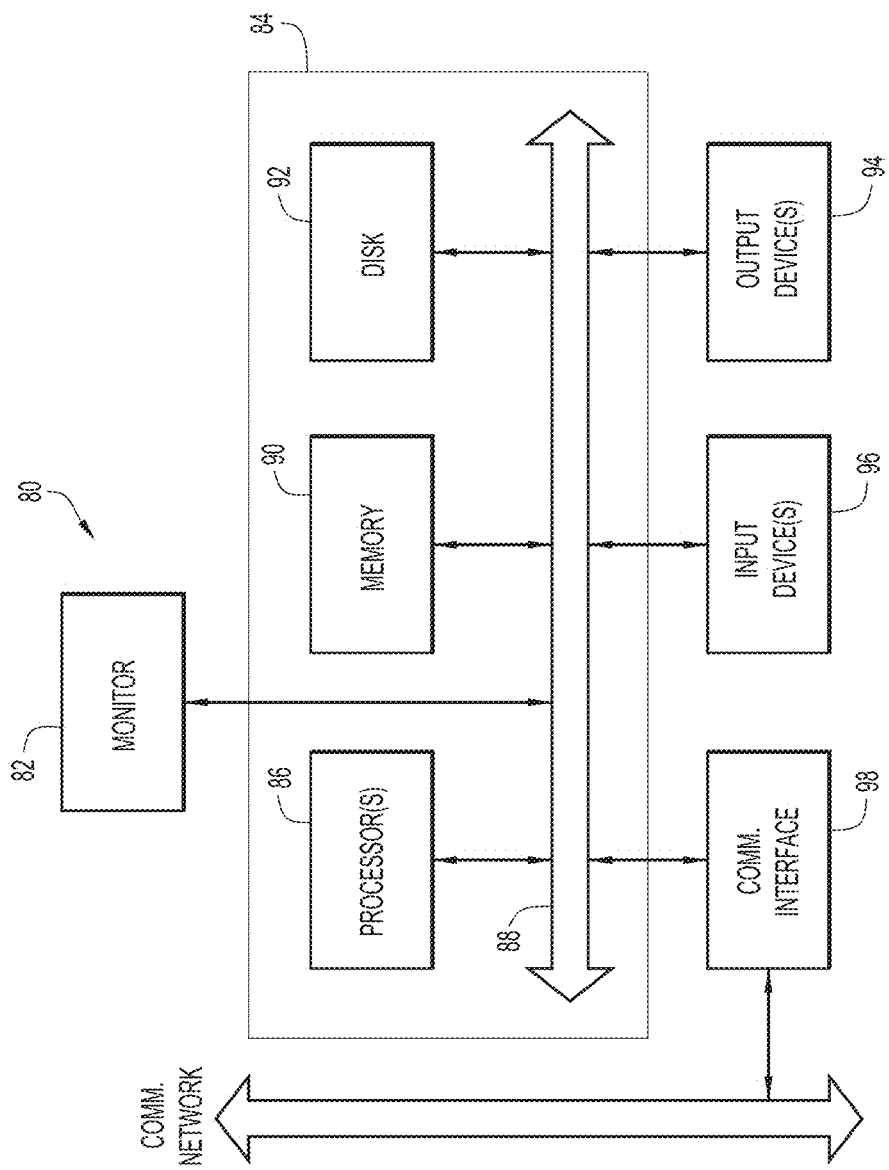
FIG. 2 is a schematic diagram of a computer system or information processing device that may be used with embodiments of the disclosure.

Referring now to FIG. 2, a block diagram of a computer system or information processing device 80 (e.g., image reconstructor 65 and/or computer 66 in FIG. 1B) is illustrated that may be incorporated into an angiographic imaging system, such as the rotational x-ray system 28 of FIGS. 1A and 1B, to provide enhanced functionality or to be used as a standalone device for motion tracking and extraction of cardiac frequency phenomena from angiographic data according to an embodiment of the present invention. Information processing device 80 may be local to or remote from rotational x-ray system 28. In one example, the functionality performed by information processing device 80 may be offered as a Software-as-a-Service (SaaS) option. SaaS refers to a software application that is stored in one or more remote servers (e.g., in the cloud) and provides one or more services (e.g., angiographic image processing) to remote users. In one embodiment, computer system 80 includes monitor or display 82, computer system 84 (which includes processor(s) 86, bus subsystem 88, memory subsystem 90, and disk subsystem 92), user output devices 94, user input devices 96, and communications interface 98. Monitor 82 can include hardware and/or software elements configured to generate visual representations or displays of information. Some examples of monitor 82 may include familiar display devices, such as a television monitor, a cathode ray tube (CRT), a liquid crystal display (LCD), or the like. In some embodiments, monitor 82 may provide an input interface, such as incorporating touch screen technologies.

Computer system 84 can include familiar computer components, such as one or more central processing units (CPUs), memories or storage devices, graphics processing units (GPUs), communication systems, interface cards, or the like. As shown in FIG. 2, computer system 84 may include one or more processor(s) 86 that communicate with a number of peripheral devices via bus subsystem 88. Processor(s) 86 may include commercially available central processing units or the like. Bus subsystem 88 can include mechanisms for letting the various components and subsystems of computer system 84 communicate with each other as intended. Although bus subsystem 88 is shown schematically as a single bus, alternative embodiments of the bus subsystem may utilize multiple bus subsystems. Peripheral devices that communicate with processor(s) 86 may include memory subsystem 90, disk subsystem 92, user output devices 94, user input devices 96, communications interface 98, or the like.

Processor(s) 86 may be implemented using one or more analog and/or digital electrical or electronic components, and may include a microprocessor, a microcontroller, an application-specific integrated circuit (ASIC), a field programmable gate array (FPGA), programmable logic and/or other analog and/or digital circuit elements configured to perform various functions described herein, such as by executing instructions stored in memory subsystem 90 and/or disk subsystem 92 or another computer program product.

Memory subsystem 90 and disk subsystem 92 are examples of physical storage media configured to store data. Memory subsystem 90 may include a number of memories including random access memory (RAM) for volatile storage of program code, instructions, and data during program execution and read only memory (ROM) in which fixed program code, instructions, and data are stored. Disk subsystem 92 may include a number of file storage systems providing persistent (non-volatile) storage for programs and data. Other types of physical storage media include floppy disks, removable hard disks, optical storage media such as compact disc—read-only memories (CD-ROMS), digital video disc (DVDs) and bar codes, semiconductor memories such as flash memories, read-only-memories (ROMS), battery-backed volatile memories, networked storage devices, or the like. Memory subsystem 90 and disk subsystem 92 may be configured to store programming and data constructs that provide functionality or features of techniques discussed herein, e.g., motion tracking system 120 and spatiotemporal reconstruction system 130 (see, FIG. 3). Software code modules and/or processor instructions that when executed by processor(s) 86 implement or otherwise provide the functionality may be stored in memory subsystem 90 and disk subsystem 92. Memory subsystem 90 may be a ion-transitory computer readable storage medium.

User input devices 96 can include hardware and/or software elements configured to receive input from a user for processing by components of computer system 80. User input devices can include all possible types of devices and mechanisms for inputting information to computer system 84. These may include a keyboard, a keypad, a touch screen, a touch interface incorporated into a display, audio input devices such as microphones and voice recognition systems, and/or other types of input devices. In various embodiments, user input devices 96 may include a computer mouse, a trackball, a track pad, a joystick, a wireless remote, a drawing tablet, a voice command system, an eye tracking system, or the like. In some embodiments, user input devices 96 are configured to allow a user to select or otherwise interact with objects, icons, text, or the like that may appear on monitor 82 via a command, motions, or gestures, such as a click of a button or the like.

User output devices 94 can include hardware and/or software elements configured to output information to a user from components of computer system 80. User output devices can include all possible types of devices and mechanisms for outputting information from computer system 84. These may include a display (e.g., monitor 82), a printer, a touch or force-feedback device, audio output devices, or the like.

Communications interface 98 can include hardware and/or software elements configured to provide unidirectional or bidirectional communication with other devices. For example, communications interface 98 may provide an interface between computer system 84 and other communication networks and devices, such as via an internet connection.

Figure 3:
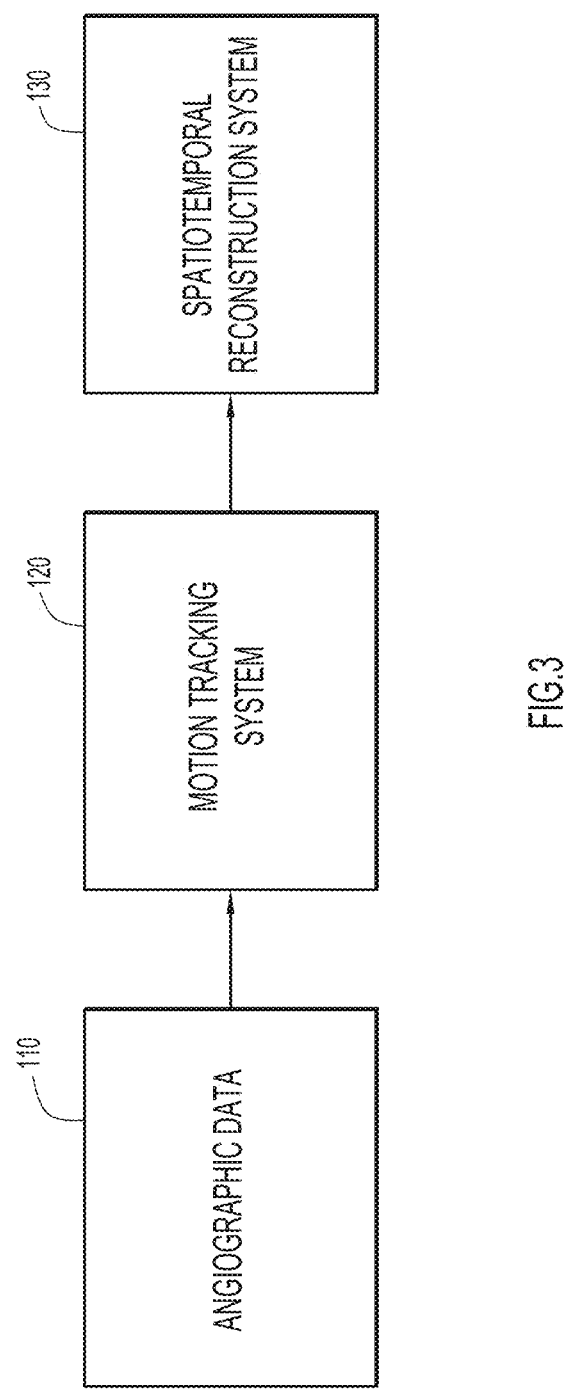
FIG. 3 is a flow chart showing an example data flow pathway for spatiotemporal reconstruction with unconstrained cardiac motion, according to embodiments of the disclosure.

FIG. 3 shows a data flow diagram, in which angiographic data 110 is obtained from a rotational x-ray system 28 at faster than cardiac rate. The angiographic data is provided to motion tracking system 120, which processes the angiographic data to generate optical flow paths that are provided to the spatiotemporal reconstruction system 130. Once the spatiotemporal reconstruction system 130 receives the optical flow paths, a spatiotemporal reconstruction is performed on unconstrained vascular objects. These embodiments are described in further detail throughout this application.

According to example embodiments of the invention, angiographic data (including angiographic image frames) may be obtained. In addition to acquiring angiographic image frames, additional cardiac signals/data may be contemporaneously acquired to serve as a cross correlation target, for purposes of performing the spatiotemporal reconstruction of the vascular pulse waves based on the techniques provided herein. For example, the additional cardiac signals/data may serve as a reference cardiac signal for phase indexing pixels in the angiographic projections. Exemplary devices for acquiring/providing a reference cardiac signal with such devices/systems in the form of a pulse oximetry system and/or an echocardiogram/electrocardiogram (EKG) system or device. In an example embodiment, the output from such a device (e.g., an EKG device) may be communicated to computer system 84 via communication interface.

Motion Tracking

According to present embodiments, optical flow techniques are utilized in connection with wavelet and other time-indexing-conserving transform angiography techniques to account for unconstrained cardiac frequency motions and to improve performance with constrained blood vessels and tissues (e.g., brain, etc.).

Optical flow techniques address the motion of objects from an image frame to the next image frame. An object (collection of pixels) moves from one frame to the next, and the displacement of the object is determined, e.g., by measuring a delta x (change with respect to x axis) and a delta y (change with respect to y axis). Based on the delta x and delta y values, the local coordinate system may be warped relative to a global coordinate system. The local coordinate system may be used to reflect the motion of a pixel along a path, and the intensities of the pixels along the path may be obtained and provided to the wavelet or other transform. Example embodiments of the invention may utilize optical flow techniques to transform the path, represented by a simple line (which may be interpolated), provided to the transform into a variable path comprising the positions of blood vessels and other structures from angiographic image frame to image frame. That is, optical flow techniques may be used to track object motion from one frame to the next frame.

To represent optical flow techniques, the following notation is introduced. Two spatial dimensions are represented as x and y, and the temporal dimension is represented as t. The intensity of the angiographic image at position x, y, t is represented as $A(x, y, t)$. The angiographic image frames are acquired at discrete time positions, $t_i$ where i is 1 ... n, where n is the number of angiographic image frames. For a particular object, such as a particular position in a blood vessel, at position x, y at frame $t_i$, the displacement of the object at the next angiographic frame $t_{i+1}$ is represented as $\Delta_x$, $\Delta_y$. Thus, stated with optical flow notation, an object at position $A(x, y, t_i)$ transitions as $$A(x,y,t_i) \rightarrow A(x+\Delta_{x,i+1}, y+\Delta_{y,i+1}, t_i+1).$$

At the successive frame $t_{i+2}$ the object transitions in position as $$A(x+\Delta_{x,i+1}, y+\Delta_{y,i+1}, t_{i+1}) \rightarrow A(x+\Delta_{x,i+1}+\Delta_{x,i+2}, y+\Delta_{y,i+1}+\Delta_{y,i+2}, t_{i+2}).$$

Each next frame is reported by the optical flow calculations as a change in position. The net position at a distance of k frames away is the recursive sum of the position changes from $t_i$ to $t_{i+k}$. The term "recursive" refers to the optical flow displacement of a position after a transition is used as being the next displacement, and these frame-wise displacements are used to construct the trajectory/path, which may be piecewise rather than necessarily following a straight line. Thus, the motion-adjusted trajectory given by the complex continuous wavelet transform of f(t) results from an integral of the optical flow calculations along the path. The Gabor wavelet equation ψ(t) extends isotropically in the positive and negative time directions. Accordingly, the trajectory for a path integral is calculated as the ordered concatenation of the optical flow integrals in both the positive t and negative t directions.

Consider an example in which, between frames $t_1$ and $t_2$, an object is displaced in the x dimension by $dx_1$ and in the y dimension by $dy_1$; also, between frames $t_2$ and $t_3$, the object is displaced in the x dimension by $dx_2$ and in the y dimension by $dy_2$. The displacement between frame $t_1$ and frame $t_3$ may be obtained by integrating the displacement between frames $t_1$ and $t_2$ and between frames $t_2$ and $t_3$. In particular, the integrated displacement in the x dimension is $dx_1+dx_2$ and the integrated displacement in the y dimension is $dy_1+dy_2$. This process may be repeated for all image frames.

Thus, for each image frame, the displacement for a given pixel may be recursively integrated in a forward temporal direction and in a reverse temporal direction to generate an optical flow trajectory for the given pixel. Use of a path integral, such as a wavelet path integral, may enable compensation for motion in unconstrained vascular objects. For example, techniques described herein may compensate for motion alias due to expansion and contraction of the heart, such that a beating heart appears still/unmoving in the processed angiographic images.

With image frames further from the center of interest, there may be a tendency of motion tracking to drift and become less accurate. This is because the motion trajectory is based on an integral of frame to frame displacements. Truly random error may compensate across motion tracking over a large number of frames, but minor bias(es) in the tracking is likely to be magnified by the integration of estimated frame-wise displacements into a path trajectory. Accordingly, when performing motion tracking in the positive or negative direction, a subset of frames may be considered with respect to a designated frame comprising a designated or central object. The designated or central object may be a pixel. For example, for a designated frame, 3-5 frames may be processed in the positive and negative direction with reference to a designated pixel (e.g., computations may become more inaccurate as distant frames are considered). In one example, an image frame of interest may be selected and the displacement for a given pixel of the image frame of interest may be determined based on image frames that are within a number (e.g., five) image frames of the image frame of interest. Once motion is determined for the designated frame, the next frame may be selected as the designated frame and the process repeated. In this way, motion determination may occur along the time series of angiograms, e.g., in a "windowed" approach.

Any suitable optical flow technique(s) may be used to measure the motion of objects from one image frame to the next. The various techniques may have comparative advantages and disadvantages. The appropriate technique for a given scenario may help exploit the motion of objects to identify cardiac frequency activity by wavelet angiography.

Sparse optical flow techniques may be used for measuring the motion of objects. A sparse optical flow technique may enable calculating only the motions of key pixels. The motions of pixels between these key pixels are interpolated from the motions of the nearby key pixels. The key pixels may be selected according to criteria such that the corresponding key pixel represents the same part of the same object on adjacent image frames. Examples of criteria for key pixels might be edges and intersections of edges. Sparse optical flow techniques may include, but are not necessarily limited to, methods described by Lucas and Kanade in "An Iterative Image Registration Techniques with an Application to Stereo Vision," Proceedings DARPA Image Understanding Workshop, April 1981, pp. 121-130, herein incorporated by reference; Harris corner adaptation as described by Harris and Stephens in "A Combined Corner and Edge Detector," Alvey Vision Conference, 1988, herein incorporated by reference; and/or derivatives of these methods.

For sparse optical flow techniques, a limited number of object locations are tracked from image frame to image frame, and the movement of the intervening object locations is interpolated. This may involve an assumption of an affine or fractional linear transformation between the two images. These techniques include the application to sequential images of geometric transforms by using common object locations on each of the images.

One example of sparse optical flow techniques depends on the identification of consistent features in two image frames and involves computing a warping that allows mapping of the features in one image frame onto the next, for example as described by Shi and Tomasi in "Good Features to Track," IEEE Conference on Computer Vision and Pattern Recognition, June 1994, herein incorporated by reference. Examples of consistent features are corners and edges, which may be identified by any suitable mathematical technique. The warping may be performed by interpolation methods such as linear or cubic spline interpolation.

Other aspects may use dense optical flow techniques that measure optical flows of all pixels from image frame to image frame. Examples include but are not necessarily limited to variational methods as derived from the use of Lagrange equations by Horn and Schunck as described in "Determining Optical Flow," Artificial Intelligence 17, 1981, 185-203 herein incorporated by reference. Horn and Schunck describe a method that assumes pixel brightness from one image frame to the next remains constant and determines a spatial distribution of pixels between one image frame and the next. The change in the spatial distribution of pixels may be interpreted to represent the motion of objects. Other approaches include dense optical flow techniques described by Farneback in "Very High Accuracy Velocity Estimation using Orientation Tensors, Parametric Motion, and Simultaneous Segmentation of the Motion Field," Proceedings Eighth IEEE International Conference on Computer Vision, July 2001, herein incorporated by reference, based on the generation of local coordinate polynomials that are convenient for describing spatial transformations from image frame to image frame. Still other approaches are based on local transforms such as the Hilbert transform to generate a monogenic signal, and which may be generalized into two dimensions to form the Riesz transform. The Riesz transform and related transforms that occur in a frequency domain may be employed to estimate a local structure tensor for tissue. This, in turn, may be employed to estimate the optical flow of biological objects from one angiographic image frame to the next. Additionally, there are directional integral transforms such as shearlets, ringlets, and curvelets that may be leveraged for optical flow information. Any of these approaches may be suitable for use with the techniques provided herein.

Still other approaches may include techniques involving deformable registration, such as the use of convolutional networks and other deep learning/machine learning/artificial intelligence methods that may be employed to estimate optical flow and in particular compute the motion of objects from one image frame to the next. Suitable examples of mathematical deformable registration may include diffeomorphism, which is derived from the field of topology. An example of a suitable open-source software package for diffeomorphism may be the Python DiPy library. This information, along with the object brightness, may be combined to estimate the motion of an object from one frame to the next. There are implementations of diffeomorphism that assume that the objects being tracked have been segmented in each of the image frames of interest. That diffeomorphism may then be computed between the segmented options in one image frame to the next. One example mathematical method that may be suitable for segmenting vascular structures and angiographic images is the Frangi filter, described by Frangi et al. in "Multiscale vessel enhancement filtering," Medical Image Computing and Computer-Assisted Intervention, 1998, herein incorporated by reference.

One suitable example of a deep learning framework may be the VoxelMorph open source software package, as described by Balakrishnan et al. in "VoxelMorph: A Learning Framework for Deformable Medical Image Registration," arXiv:1809.05231 [cs.CV], Sep. 1, 2019, herein incorporated by reference. VoxelMorph employs a deep learning neural network to compute the diffeomorphism between objects in respective image frames. In another suitable example of a deep learning framework, neural networks may be employed to interpolate a higher video frame rate cardiac angiogram from one that is captured at a lower rate. Software packages, such as the Depth-Aware video frame INterpolation (DAIN) network model, described by Bao et al. in "Depth-Aware Video Frame Interpolation," IEEE Conference on Computer Vision and Pattern Recognition, 2019, herein incorporated by reference, may use variations of convolutional neural networks for video frame interpolation.

In other embodiments, steerable filters may be employed to detect local orientation in images. This approach may be used to estimate a motion trajectory. Steerable filters may comprise a convolution kernel, and may be used for image enhancement and feature extraction. For example, a given image frame may have a set of steerable filters corresponding to different objects in the image if the different objects are moving in different directions. Each direction of motion may be represented by a steerable filter that encodes and filters for a particular direction of motion. In still other examples, any suitable supervised or unsupervised machine learning model may be used (e.g., mathematical/statistical models, classifiers, feed-forward, recurrent or other neural networks, etc.).

The above list includes examples of the optical flow techniques that may be adapted for the purpose of motion-compensated wavelet or time-indexing-conserving angiography. Present embodiments are not necessarily limited to the above-referenced optical flow techniques and may include any suitable optical flow technique. For example, the image displacement function provided by the Mathematica® environment (ImageDisplacements[ ]), as described by Wolfram Research in "ImageDisplacements," Wolfram Language function, https://reference.wolfram.com/language/ref/ImageDisplacements.html (2016), herein incorporated by reference, may be employed for performing wavelet angiography with motion compensation by optical flow techniques.

Furthermore, multiple objects may be tracked, each with a respective local coordinate system. The motion of all objects may be reversed (in a bookkeeping sense) for the wavelet calculation. In one example, motion of all pixels may be estimated. In a sparse optical flow technique, the motions of key pixels that may be computationally efficient to track may be measured, and the motions of pixels between the key pixels may be interpolated. In a dense optical flow technique, the motions of all pixels may be measured. A deep learning system based on AI object recognition may use approaches similar to sparse optical flow techniques. Some deep learning methods may be based on training against object recognition and/or pixel-wise motion. This may be similar to dense optical flow techniques.

Wavelet Angiography/Spatiotemporal Reconstruction

Wavelet angiography employs complex-valued wavelet transforms to generate a spatiotemporal reconstruction of cardiac frequency phenomena in an angiogram obtained at faster than cardiac frequency. A wavelet transform is founded on a line integral.

For a signal f(t) and mother wavelet $\psi$, the complex continuous wavelet transform of f(t) is given by the equation:

$$W(u, s) = \frac{\int_{-\infty}^{\infty} f(t) \varphi^*\left(\frac{t-u}{s}\right) dt}{\sqrt{s}} \quad (1)$$

where s is a wavelet scale, as above, u is the wavelet translation parameter, and the superscript * represents complex conjugation. In wavelet angiography, the Gabor wavelet may be selected to serve as the particular wavelet $\psi$. The Gabor (variably termed Morlet) family of $\psi$s offer explicit balancing of frequency and temporal resolution. This family is based on the equation:

$$\varphi(t) = \frac{1}{\sqrt[4]{\pi}} e^{-\frac{t^2}{2}} e^{nit}. \quad (2)$$

As described above, the signal at cardiac frequency in an angiogram is exploited to increase the sensitivity of angiographic imaging to arterial anatomy and to venous anatomy, allowing identification of altered and pathological patterns of circulation such as vessel occlusions and other blood flow states at lower x-ray doses and/or at lower intravascular contrast doses. Additionally, it may allow for the separation of arterial from venous anatomy without navigating and injecting a catheter into the distal arterial tree. The coherence at cardiac frequency among circulatory sub-systems may be exploited to allow the anatomic identification of arterial anatomy and venous anatomy at lower x-ray doses and at lower intravascular contrast doses.

In carrying out the methods described herein, the angiographic data may be recorded using a digital detector device, such as those commercially available as part of scanning devices available from manufacturers such as Philips and Siemens. The digital data are then imported into a computer memory. After the import into computer memory of an angiogram (in the absence of motion alias), the spatiotemporal reconstruction of cardiac frequency angiographic phenomena may be obtained. In one example, spatiotemporal reconstruction may be performed in accordance with techniques described in U.S. Pat. No. 10,123,761, issued Nov. 13, 2018; U.S. patent application Ser. No. 16/784,125, filed Feb. 6, 2020; U.S. patent application Ser. No. 16/784,073, filed Feb. 6, 2020; U.S. patent application Ser. No. 16/813,513, filed Mar. 9, 2020; U.S. patent application Ser. No. 16/832,695, filed Mar. 27, 2020; and/or U.S. patent application Ser. No. 16/841,247, filed Apr. 6, 2020; each of which is hereby incorporated by reference.

The angiographic data may be imported into computer memory and reformatted with the processor in memory to give an array of time signals. A complex valued wavelet transform is applied by the processor to each pixel-wise time signal, giving an array of wavelet transforms. The pixel-wise wavelet transforms are filtered for cardiac frequency by the processor. This is done by setting to zero all wavelet coefficients that do not correspond to cardiac wavelet scale (in the field of wavelets this term corresponds to the concept of cardiac frequency). The pixel-wise wavelet transform data are inverse wavelet transformed by the processor into the time domain and reformatted in computer memory into pixels. Each data element (voxel) in this three dimensional grid is a complex valued number.

Each frame can be rendered as an image with a brightness hue color model to represent the complex datum in each pixel by the processor. Cardiac frequency magnitude is represented as brightness and phase as hue. The q images may be rendered as motion cine by the processor or they may be stored as a video file format by the processor. For example, one or more images may be provided as a cine video sequence. In one example, the object motions may be applied in reverse to all of the pixels in every image to create a new video sequence where all objects appear to be still. This video may be processed with wavelet calculations to identify the cardiac frequency phenomena. The object motions may then be applied in the forward sense to restore the object motions to the wavelet-transformed result.

If the wavelet transform has a frequency resolution of, e.g., ten image frames, then the motions may only need to be calculated for a neighborhood of ten image frames. This may be repeated for every image frame. If there is error drift in the estimation of motion, then the error from the drift may be limited to the drift that may occur in those ten frames as opposed to the aggregate drift from hundreds of frames in the angiographic sequence.

Any suitable transform, operable on complex numbers that retain time indexing after transformation into the frequency domain, and capable of extracting the spatiotemporal reconstruction of cardiac frequency angiographic phenomena is contemplated for use with the present techniques.

Figure 4A:
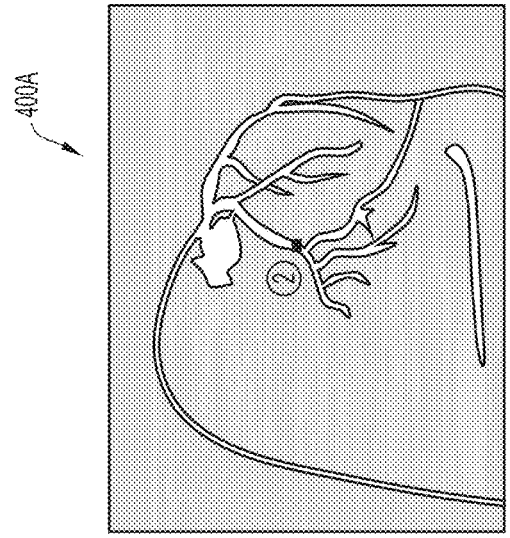
FIGS. 4A-4C are angiogram image frames showing an example of unconstrained vascular motion (e.g., blood vessel motion) in a pig coronary artery.
Figure 4B:
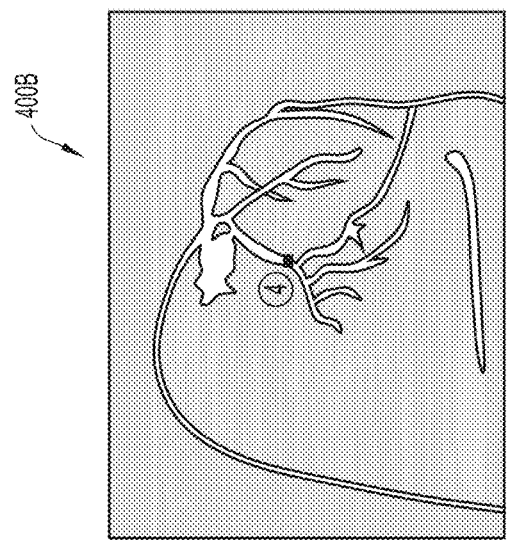
Figure 4C:
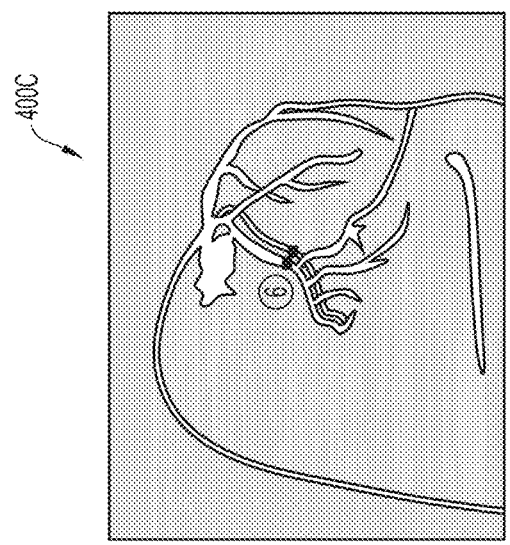

FIGS. 4A and 4B show two successive angiogram image frames 400A and 400B (one frame apart), wherein angiogram image frame 400A and angiogram image frame 400B are selected from a pig coronary artery angiogram obtained at 30 Hz (which is faster than cardiac frequency). The same location on the same coronary artery (termed the Left Anterior Descending Artery) labeled coronary artery location 2 and coronary artery location 4 is indicated on angiogram image frames 400A and 400B, respectively. The spatial displacement of the same coronary artery location between angiogram image frames 400A and 400B illustrates the magnitude of motion. FIG. 4C shows a superposition 400C of angiogram image frames 400A and 400B. The pixels 6 in superposition 400C are offset, indicating motion that has occurred from angiogram image frame 400A to angiogram image frame 400B.

Figure 5:
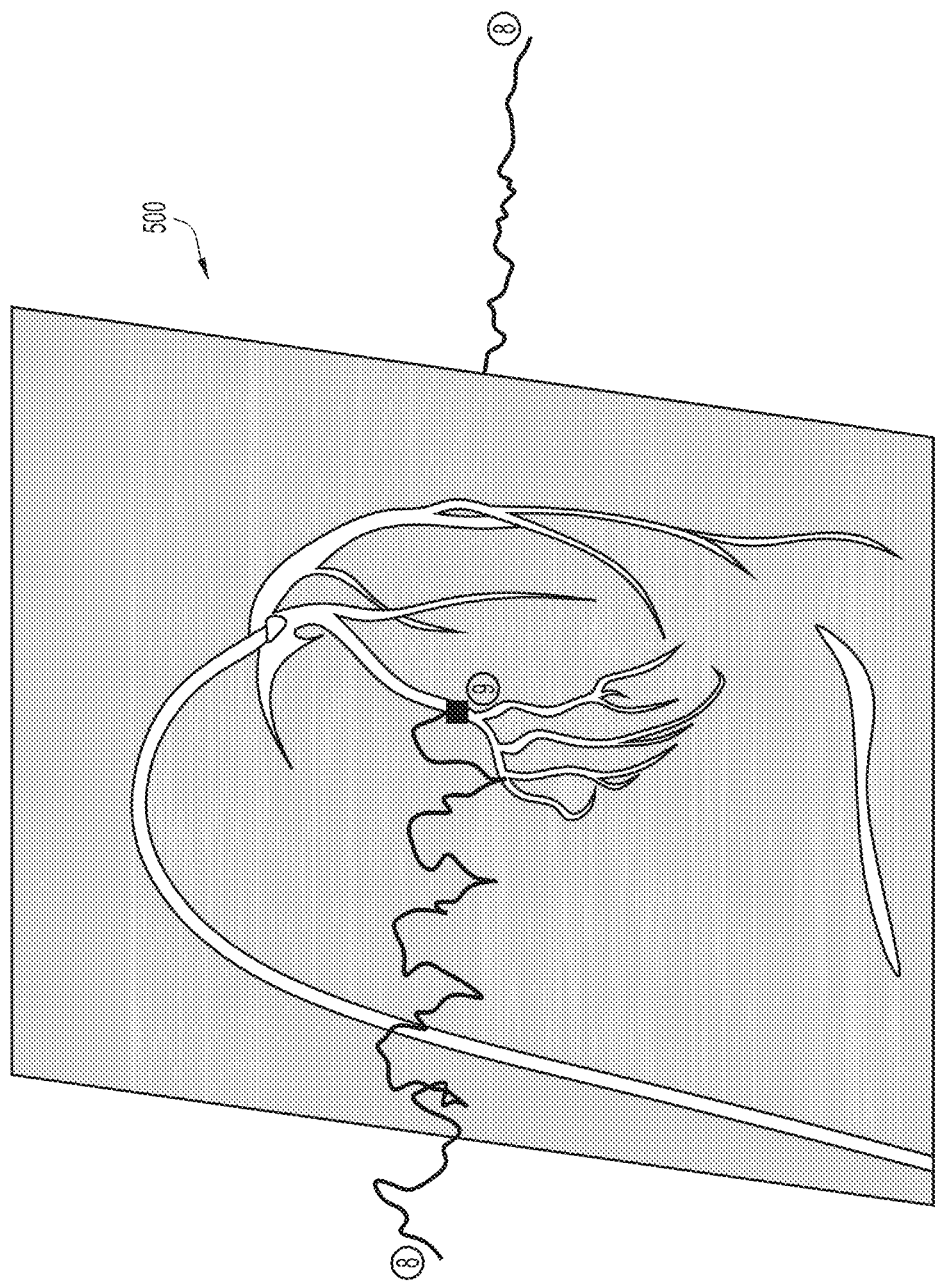
FIG. 5 shows an example of an optical flow path in relation to an example angiogram image frame for a given coronary artery, according to an embodiment of the disclosure.

FIG. 5 shows an example optical flow path for a selected pixel 9 in relation to a specific image frame 500 of an optical angiogram. In the example, the image frame 500 has a particular pixel of interest within a blood vessel, referred to as an optical flow pixel 9. An optical flow trajectory 8 is shown that extends in both temporal directions from the optical flow pixel 9. Optical flow trajectory 8 represents the path of the same pixel 9 as the heart is beating. This trajectory represents the integration path for the wavelet transform (e.g., Gabor wavelet transform). This shows the motion track across the entire angiographic sequence as the contrast bolus is injected and then dissipates. Optical flow pixel 9 moves at cardiac frequency, however, this pixel does not follow exactly the same trajectory from one heartbeat to the next as there may be variation in heart muscle contraction and as well as error from motion tracking. The optical flow path is the path along which the wavelet transform and inverse transform is performed to generate a spatiotemporal reconstruction.

This process is repeated for each angiographic image frame, e.g., to produce a sequence of motion adjusted Gabor wavelet transformations. The Gabor wavelet transformations may be filtered at cardiac frequency and inverse transformed. For the inverse wavelet transformation, only the wavelet scale corresponding to cardiac frequency is retained.

Each pixel grid location x, y, t is returned as a complex-valued datum, which may be rendered as an image using any suitable scheme, e.g., a brightness-hue model (e.g., wherein complex-valued magnitude is rendered as brightness and cardiac frequency phase as hue), etc. In one example, one or more techniques described in U.S. Pat. No. 10,123,761 may be utilized for rendering the image.

The angiographic images are image intensity numbers on a discrete grid according to the number of pixels in the horizontal x and vertical y directions. However, optical flow trajectories may return object position changes as fractional pixel values. Hence, in an embodiment, the discrete angiographic image grid may be converted to a spline interpolated data volume that allows access to fractional pixel values by interpolation.

Figure 6B:
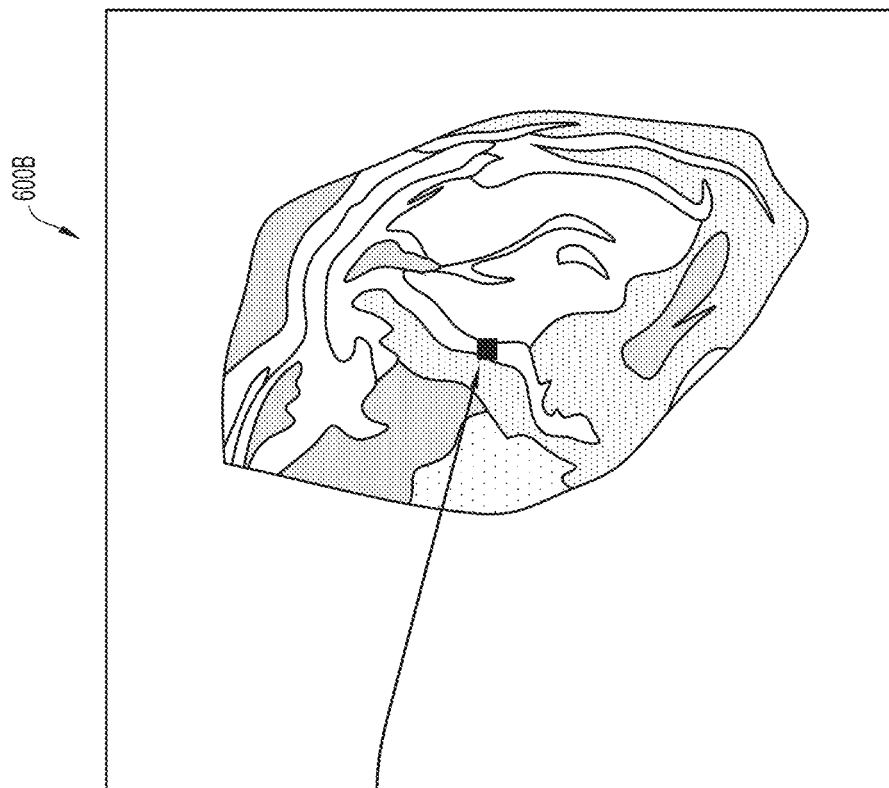
FIGS. 6A and 6B are example angiogram image frames showing wavelet angiography representations after accounting for unconstrained vascular motion, such as coronary artery motion, according to embodiments of the disclosure.
Figure 6A:
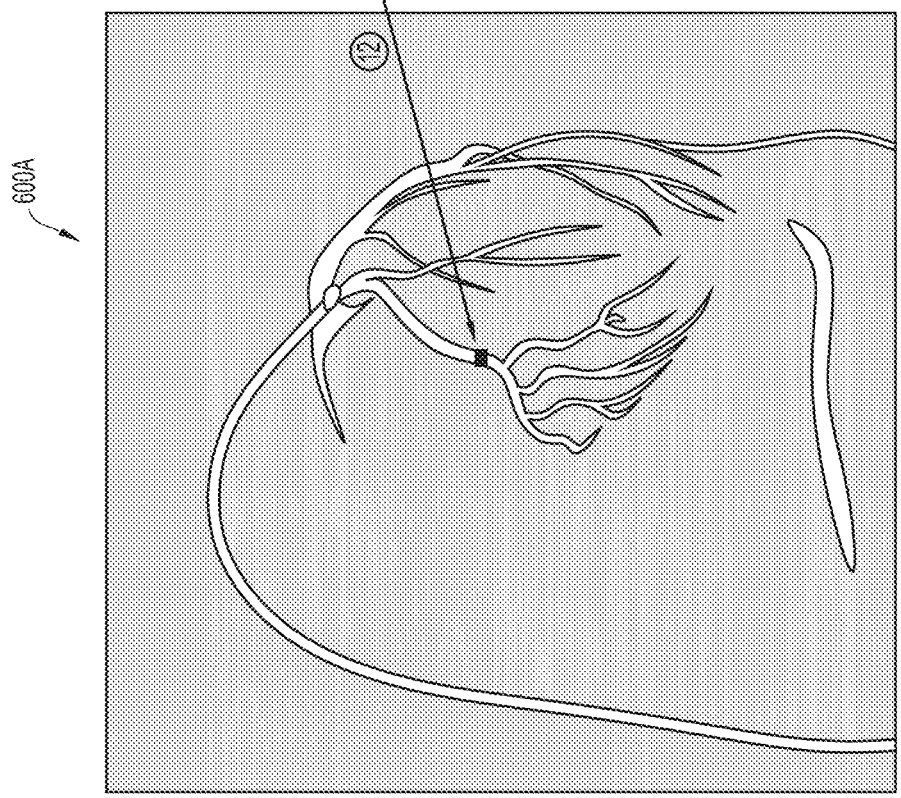

The result of an example motion compensated wavelet angiogram transform is shown in FIGS. 6A-6B. A raw angiogram image frame 600A on the left (FIG. 6A) is shown and the results after motion processing and spatiotemporal reconstruction are shown on the right wavelet angiogram frame 600B (FIG. 6B). The matching pixel 12 represents the same location on the same vessel as labeled.

Figure 7:
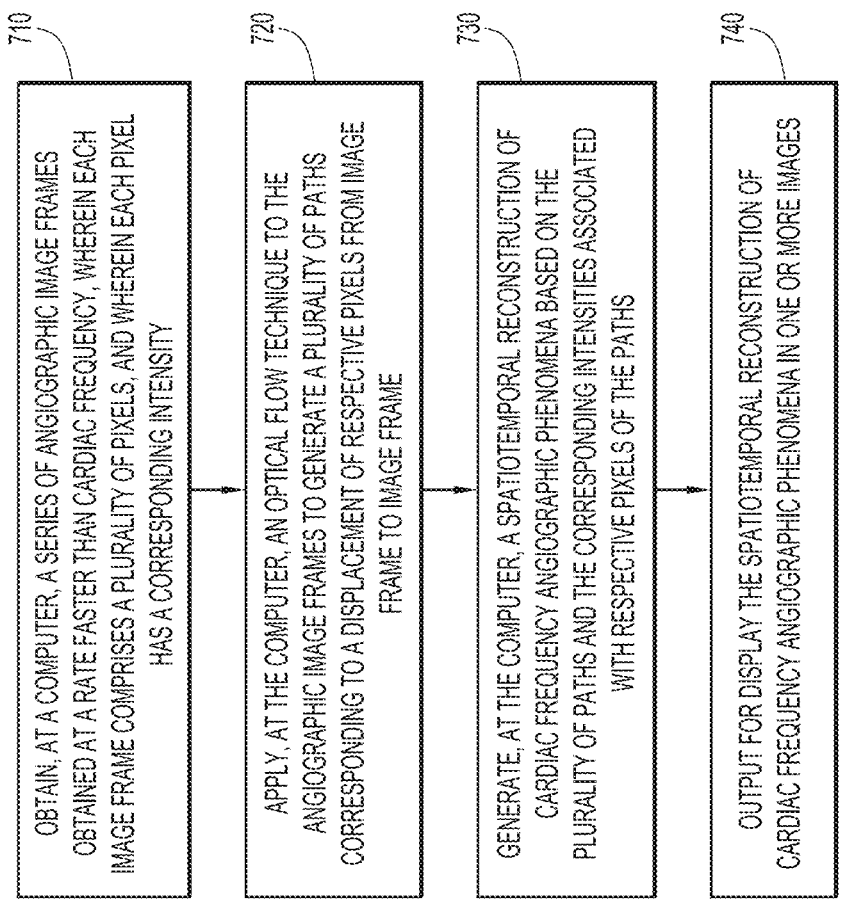
FIG. 7 is a flowchart showing techniques for reconstructing cardiac frequency phenomena in angiographic data for unconstrained vascular objects according to an example embodiment of the disclosure.

FIG. 7 is a flow chart of operations for obtaining and processing data with large scale cardiac motion, according to an embodiment of the techniques described herein. At operation 710, a series of angiographic image frames is obtained from an angiographic study at a rate faster than cardiac frequency. For example, the angiographic data image frames may be obtained using a rotational x-ray angiography system as shown in FIGS. 1A and 1B and acquired or received by a computer in the angiography system or by a standalone computer. The angiographic image frames may include a time series of angiographic image frames. Each image frame may be associated with a particular time, t, and may include a plurality of pixels. Each pixel may be located at an x-y position in the image frame and have a corresponding brightness or intensity.

At operation 720, an optical flow technique is applied to the angiographic image frames to generate a plurality of paths corresponding to a displacement of respective pixels from image frame to image frame. For example, motion tracking may be performed on image pixels by the computer to allow measurement at cardiac frequency of vascular pulses in a moving heart vessel, tissue, or organ. The image may represent a global coordinate system, and motion may be tracked with regard to a local coordinate system. For example, the moving blood vessel, organ, or tissue may be tracked with respect to the local coordinate system. Thus, pixels of the image may be transformed to the local coordinate system, and a track or path may be determined for the transformed pixel to track the position of the pixel over time.

At operation 730, a spatiotemporal reconstruction of cardiac frequency angiographic phenomena is generated by the computer based on the plurality of paths and the corresponding intensities associated with respective pixels of the paths. For example, the plurality of tracks or paths generated by the computer in operation 720 may be fed into a wavelet transform or other transform that preserves time indexing. The pixel-wise transforms may then be filtered for cardiac frequency by the computer. This may be done by setting to zero all transform coefficients that do not correspond to cardiac wavelet scale (in the field of wavelets this term corresponds to the concept of cardiac frequency). The pixel-wise transforms data may then be inverse transformed by the computer into the time domain and reformatted in computer memory into pixels. Each data element (voxel) in this three dimensional grid may be a complex valued number.

At operation 740, the spatiotemporal reconstruction of cardiac frequency angiographic phenomena is outputted for display in one or more images. For example, each frame may be rendered by the computer as an image with a brightness hue color model to represent the complex datum in each pixel. Cardiac frequency magnitude may be represented as brightness and phase as hue. The image may be displayed on a screen, stored as an image file, and/or printed. The q images may be rendered as motion cine by the computer or they may be stored as a video file format by the processor.

The techniques described herein are not necessarily limited to cardiac applications. Other applications may include optical angiography. For example, optical angiography of the retina in an awake patient may capture saccadic movements of the eye. The techniques described herein may be used to compensate for this type of motion. Other motion sources that could be compensated for by this technique include but are not necessarily limited to breathing motions, and spontaneous voluntary or involuntary motions. These techniques may be applied to any suitable target/body part (e.g., blood vessel, organ, etc.) that experience large-scale or unconstrained motion.

Techniques described herein may be implemented in conjunction with administration of an effective amount of contrast to visualize the object. When motion determination via optical flow paths moves in both a forward and reverse direction, these techniques may be suitable for measuring the motion of the object in intermediate image frames (e.g., image frames surrounded by other image frames in the image sequence). However, it will be appreciated that the techniques described herein may also be suitable for measuring object motion at the start and the end of the image sequence, and may be used with or without contrast.

The present invention may include a method, system, device, and/or a computer program product at any possible technical detail level of integration. The computer program product may include a computer readable storage medium (or media) having computer readable program instructions thereon for causing a processor to carry out aspects of the present invention.

Computer readable program instructions described herein can be downloaded to respective computing/processing devices from a computer readable storage medium or to an external computer or external storage device via a network, for example, the Internet, a local area network, a wide area network and/or a wireless network. The network may comprise conductive transmission cables, optical transmission fibers, wireless transmission, routers, firewalls, switches, gateway computers and/or edge servers. A network adapter card or network interface in each computing/processing device may receive computer readable program instructions from the network and forward the computer readable program instructions for storage in a computer readable storage medium within the respective computing/processing device.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The above description is for the purpose of teaching the person of ordinary skill in the art how to practice the subject of the present application, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for extracting cardiac frequency angiographic phenomena for an unconstrained vascular object from an angiographic study, the method comprising:
    obtaining, at a computer, a series of angiographic image frames obtained at a rate faster than cardiac frequency, wherein each image frame comprises a plurality of pixels, and wherein each pixel has a corresponding intensity;
    applying, at the computer, an optical flow technique to the angiographic image frames to generate a plurality of paths corresponding to a displacement of respective pixels from image frame to image frame, wherein applying the optical flow technique comprises, for each image frame, recursively integrating the displacement for a given pixel in a forward temporal direction and in a reverse temporal direction to generate an optical flow trajectory for the given pixel;
    generating, at the computer, a spatiotemporal reconstruction of cardiac frequency angiographic phenomena based on the plurality of paths and the corresponding intensities associated with respective pixels of the paths; and
    outputting for display the spatiotemporal reconstruction of cardiac frequency angiographic phenomena in one or more images.

2. The method of claim 1, further comprising:
    selecting an image frame of interest; and
    determining the displacement for a given pixel of the image frame of interest based on image frames that are within a number of image frames of the image frame of interest.

3. The method of claim 1, wherein applying the optical flow technique includes:
    applying a dense optical flow technique that measures optical flows of the plurality of pixels from image frame to image frame.

4. The method of claim 1, wherein applying the optical flow technique includes:
    applying a sparse optical flow technique including:
        tracking a limited number of object locations from image frame to image frame; and
        interpolating a movement of intervening object locations.

5. The method of claim 1, wherein applying the optical flow technique includes:
determining each path based on a local coordinate system.

6. The method of claim 1, further comprising:
providing the one or more images as a cine video sequence.

7. A system comprising:
a communications interface configured to obtain a series of angiographic image frames obtained at a rate faster than cardiac frequency, wherein each image frame comprises a plurality of pixels, and wherein each pixel has a corresponding intensity; and
one or more processors coupled to the communications interface, wherein the one or more processors are configured to:
apply an optical flow technique to the angiographic image frames to generate a plurality of paths corresponding to a displacement of respective pixels from image frame to image frame, wherein applying the optical flow technique comprises for each image frame, recursively integrate the displacement for a given pixel in a forward temporal direction and in a reverse temporal direction to generate an optical flow trajectory for the given pixel;
generate a spatiotemporal reconstruction of cardiac frequency angiographic phenomena based on the plurality of paths and the corresponding intensities associated with respective pixels of the paths; and
output for display the spatiotemporal reconstruction of cardiac frequency angiographic phenomena in one or more images.

8. The system of claim 7, wherein the one or more processors are further configured to:
select an image frame of interest; and
determine the displacement for a given pixel of the image frame of interest based on image frames that are within a number of image frames of the image frame of interest.

9. The system of claim 7, wherein the one or more processors are further configured to:
apply a dense optical flow technique that measures optical flows of the plurality of pixels from image frame to image frame.

10. The system of claim 7, wherein the one or more processors are further configured to:
apply a sparse optical flow technique including:
tracking a limited number of object locations from image frame to image frame; and
interpolating a movement of intervening object locations.

11. The system of claim 7, wherein the one or more processors are further configured to:
determine each path based on a local coordinate system.

12. The system of claim 7, wherein the one or more processors are further configured to:
provide the one or more images as a cine video sequence.

13. One or more non-transitory computer readable storage media encoded with instructions that, when executed by a processor, cause the processor to:
obtain a series of angiographic image frames obtained at a rate faster than cardiac frequency, wherein each image frame comprises a plurality of pixels, and wherein each pixel has a corresponding intensity;
apply an optical flow technique to the angiographic image frames to generate a plurality of paths corresponding to a displacement of respective pixels from image frame to image frame, wherein applying the optical flow technique comprises for each image frame, recursively integrate the displacement for a given pixel in a forward temporal direction and in a reverse temporal direction to generate an optical flow trajectory for the given pixel;
generate a spatiotemporal reconstruction of cardiac frequency angiographic phenomena based on the plurality of paths and the corresponding intensities associated with respective pixels of the paths; and
output for display the spatiotemporal reconstruction of cardiac frequency angiographic phenomena in one or more images.

14. The one or more non-transitory computer readable storage media of claim 13, wherein the instructions further cause the processor to:
select an image frame of interest; and
determine the displacement for a given pixel of the image frame of interest based on image frames that are within a number of image frames of the image frame of interest.

15. The one or more non-transitory computer readable storage media of claim 13, wherein the instructions further cause the processor to:
apply a dense optical flow technique that measures optical flows of the plurality of pixels from image frame to image frame.

16. The one or more non-transitory computer readable storage media of claim 13, wherein the instructions further cause the processor to:
apply a sparse optical flow technique including:
tracking a limited number of object locations from image frame to image frame; and
interpolating a movement of intervening object locations.

17. The one or more non-transitory computer readable storage media of claim 13, wherein the instructions further cause the processor to:
provide the one or more images as a cine video sequence.

* * * * *